US007045133B2

(12) United States Patent
Achen et al.

(10) Patent No.: US 7,045,133 B2
(45) Date of Patent: May 16, 2006

(54) VEGF-D/VEGF-C/VEGF PEPTIDOMIMETIC INHIBITOR

(75) Inventors: Marc G. Achen, North Melbourne (AU); Richard A. Hughes, North Melbourne (AU); Steven Stacker, North Fitzroy (AU); Angela Cendron, Campbellfield (AU)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 09/761,636

(22) Filed: Jan. 18, 2001

(65) Prior Publication Data

US 2002/0065218 A1 May 30, 2002

Related U.S. Application Data

(60) Provisional application No. 60/176,293, filed on Jan. 18, 2000, provisional application No. 60/204,590, filed on May 16, 2000.

(51) Int. Cl.
*A61K 38/12* (2006.01)
*A61K 38/04* (2006.01)
*A61K 39/00* (2006.01)
(52) U.S. Cl. .......................... 424/185.1; 514/9; 514/11; 514/19; 530/317; 530/321
(58) Field of Classification Search .................. 514/9, 514/10, 11, 19; 424/185.1; 530/317, 321, 530/323
See application file for complete search history.

(56) References Cited

U.S. PATENT DOCUMENTS 5,932,540 A   8/1999   Hu et al.
5,935,820 A   8/1999   Hu et al.
6,383,484 B1 * 5/2002  Achen et al.

FOREIGN PATENT DOCUMENTS

| EP | 0467701 | 1/1992 |
|---|---|---|
| WO | WO 95/34312 | 12/1995 |
| WO | WO 98/07832 | 2/1998 |
| WO | WO9807832 | 2/1998 |
| WO | WO 99/40947 | 8/1999 |
| WO | WO 99/66954 | 12/1999 |
| WO | WO 00/75176 | 12/2000 |

OTHER PUBLICATIONS

Attwood et al, The Babel of Bioinformatics, 2000, Science vol. 290 No. 5491: 471-473.*
Skolnick et al., From genes to protein structure and function: novel applications of computational approaches in the genomic era, Jan., 2000, TIBTECH 18: 34-39.*
Potgens et al, J Biol Chem 269(52): 32879-85, Dec. 1994.*
Stacker et al, J Biol Chem 274(45): 32127-26; Nov. 1999.*
Ngo et al, 1994, The Protein Folding Problem and Tertiary Structure Prediction, pp. 492-495.*
Stacker et al, J Biol Chem 274(49): 34884-92, 1999.*
Walsh et al, Protein Engineering 10(4): 389-98, 1997.*
Kiba et al, J Biol Chem 278(15): 13453-61, 2003.*
Baldwin et al, J Biol Chem 276(22): 19166-19171, 2001.*
Yamada et al, Genomics 42(3):483-8; Jun. 15, 1997.*
Le et al, Accession No. T25674, Oct. 1999.*
Arja Kaipainen, "Expression of the fms-like tyrosine kinase 4 gene becomes restricted to lymphathic endothelium during development" Proc. Natl. Acad. Sci, USA, Apr. 1995, vol. 92: 3566-70.
James Lee, "Vascular endothelial growth factor-related protein: A ligand and specific activator of the tyrosine kinase receptor Flt4" Proc. Natl. Acad. Sci, USA, Mar. 1996, vol. 93: 1988-92.
J. Taipale, "Vascular Endothelial Growth Factor Receptor-3" Current Topics in Microbiology and Immunology, vol. 237, 1999, vol. 237: 85-96.
Arja Kaipainen, "Enhanced Expression of the Tie Receptor Tyrosine Kinase Messenger RNA in the Vascular Endothelium of Metastatic Melanomas" Cancer Research, Dec. 1994, vol. 54: 6571-77.
Vladimir Joukov, "A novel vascular endothelial growth factor, VEGF-C, is a ligand for the Flt4 (VEGFR-3) and KDR (VEGFR-2) receptor tyrosine kinases" The EMBO Journal, 1996, vol. 15(2):290-298.
Marc G. Achen, "Monoclonal antibodies to vascular endothelial growth factor-D block its interactions wtih both VEGF receptor-2 and VEGF receptor-3" Eur. J. Biochemistry, Feb. 2000, vol. 267: 2505-15.
Marc G. Achen, "Vascular endothelial growth factor D (VEGF-D) is a ligand for the tyrosine kinases VEGF receptor 2 (Flk1) and VEGF receptor 3 (Flt4)" Proc. National Acad. of Science, Jan. 1998, vol. 95: 548-553.
Steven Stacker, "VEGF-D promotes the metastatic spread of tumor cells via the lymphatics" Nature Medicine, Feb. 2001, vol. 7(2): 186-191.

* cited by examiner

*Primary Examiner*—Christina Chan
*Assistant Examiner*—Phuong Huynh
(74) *Attorney, Agent, or Firm*—Crowell & Moring LLP

(57) ABSTRACT

Monomeric monocyclic peptide inhibitors and dimeric bicyclic peptide inhibitors based on exposed loop fragments of a growth factor protein, such as loop 1, 2 or 3 of VEGF-D, and methods of making them are described as well as pharmaceutical compositions containing them and methods utilizing them.

33 Claims, 25 Drawing Sheets

VEGF-D/VEGF-C/VEGF PEPTIDOMIMETIC INHIBITOR

CROSS REFERENCE TO RELATED APPLICATIONS

This application claims priority of U.S. Provisional Application Nos. 60/176,293, filed Jan. 18, 2000 and 60/204,590, filed May 16, 2000.

BACKGROUND OF THE INVENTION

The invention generally relates to small, conformationally-constrained peptide inhibitors of members of the VEGF family of compounds. Specifically, the invention provides a purified monomeric monocyclic peptide inhibitor and a purified dimeric bicyclic peptide inhibitor, both based on loop 1, 2 or 3 of VEFG-D as well as methods of making them. The invention also relates to pharmaceutical compositions and methods utilizing these peptide inhibitors.

The two major components of the mammalian vascular system are the endothelial and smooth muscle cells. The endothelial cells form the lining of the inner surface of all blood vessels and lymphatic vessels in the mammal. The formation of new blood vessels can occur by two different processes, vasculogenesis or angiogenesis (for review see Risau, W., *Nature* 386: 671–674, 1997). Vasculogenesis is characterized by in situ differentiation of endothelial cell precursors to mature endothelial cells and association of these cells to form vessels, such as occurs in the formation of the primary vascular plexus in the early embryo. In contrast, angiogenesis, the formation of blood vessels by growth and branching of pre-existing vessels, is important in later embryogenesis and is responsible for the blood vessel growth which occurs in the adult. Angiogenesis is a physiologically complex process involving proliferation of endothelial cells, degradation of extracellular matrix, branching of vessels and subsequent cell adhesion events. In the adult, angiogenesis is tightly controlled and limited under normal circumstances to the female reproductive system. However angiogenesis can be switched on in response to tissue damage. Importantly, solid tumors are able to induce angiogenesis in surrounding tissue, thus sustaining tumor growth and facilitating the formation of metastases (Folkman, J., *Nature Med.* 1: 27–31, 1995). The molecular mechanisms underlying the complex angiogenic processes are far from being understood.

Angiogenesis is also involved in a number of pathological conditions, where it plays a role or is involved directly in different sequelae of the disease. Some examples include neovascularization associated with various liver diseases, neovascular sequelae of diabetes, neovascular sequelae to hypertension, neovascularization in post-trauma, neovascularization due to head trauma, neovascularization in chronic liver infection (e.g. chronic hepatitis), neovascularization due to heat or cold trauma, dysfunction related to excess of hormone, creation of hemangiomas and restenosis following angioplasty. In arthritis, the pathological condition occurs because new capillaries invade the joint and destroy the cartilage. In diabetes, one pathological condition is caused by new capillaries in the retina invading the vitreous humour, causing bleeding and blindness (Folkman and Shing, *J. Biol. Chem.* 267:10931–10934, 1992). The role of angiogenic factors in these and other diseases has not yet been clearly established.

Because of the crucial role of angiogenesis in so many physiological and pathological processes, factors involved in the control of angiogenesis have been intensively investigated. A number of growth factors have been shown to be involved in the regulation of angiogenesis. These include the fibroblast growth factors (FGFs) the platelet-derived growth factors (PDGFs), the transforming growth factor alpha (TGFα), and the hepatocyte growth factor (HGF). See for example Folkman et al., *J. Biol. Chem.*, 267: 10931–10934, 1992 for a review.

It has been suggested that a particular family of endothelial cell-specific growth factors, the vascular endothelial growth factors (VEGFs), and their corresponding receptors are primarily responsible for stimulation of endothelial cell growth and differentiation and for certain functions of the differentiated cells. These factors are members of the PDGF/VEGF family, and appear to act primarily via endothelial receptor tyrosine kinases (RTKs). The PDGF/VEGF family of growth factors belongs to the cystine-knot superfamily of growth factors, which also includes the neurotrophins and transforming growth factor-β.

Eight different proteins have been identified in the PDGF/VEGF family, namely two PDGFs (A and B), VEGF and five members that are closely related to VEGF. The five members closely related to VEGF are: VEGF-B, described in International Patent Application PCT/US96/02957 (WO 96/26736) and in U.S. Pat. Nos. 5,840,693 and 5,607,918 by Ludwig Institute for Cancer Research and The University of Helsinki; VEGF-C or VEGF2, described in Joukov et al., *EMBO J.*, 15: 290–298, 1996, Lee et al., *Proc. Natl. Acad. Sci. USA*, 93: 1988–1992, 1996, and U.S. Pat. Nos. 5,932,540 and 5,935,540 by Human Genome Sciences, Inc; VEGF-D, described in International Patent Application No. PCT/US97/14696 (WO 98/07832), and Achen et al., *Proc. Natl. Acad. Sci. USA*, 95: 548–553, 1998; the placenta growth factor (PlGF), described in Maglione et al., Proc. Natl. Acad. Sci. USA, 88: 9267–9271, 1991; and VEGF3, described in International Patent Application No. PCT/US95/07283 (WO 96/39421) by Human Genome Sciences, Inc. Each VEGF family member has between 30% and 45% amino acid sequence identity with VEGF. The VEGF family members share a VEGF homology domain which contains the six cysteine residues which form the cystine-knot motif. Functional characteristics of the VEGF family include varying degrees of mitogenicity for endothelial cells, induction of vascular permeability and angiogenic and lymphangiogenic properties.

Vascular endothelial growth factor (VEGF) is a homodimeric glycoprotein that has been isolated from several sources. Alterative mRNA splicing of a single VEGF gene gives rise to five isoforms of VEGF. VEGF shows highly specific mitogenic activity for endothelial cells. VEGF has important regulatory functions in the formation of new blood vessels during embryonic vasculogenesis and in angiogenesis during adult life (Carmeliet et al., *Nature,* 380: 435–439, 1996; Ferrara et al., *Nature,* 380: 439–442, 1996; reviewed in Ferrara and Davis-Smyth, *Endocrine Rev.,* 18: 4–25, 1997). The significance of the role played by VEGF has been demonstrated in studies showing that inactivation of a single VEGF allele results in embryonic lethality due to failed development of the vasculature (Carmeliet et al., *Nature,* 380: 435–439, 1996; Ferrara et al., *Nature,* 380: 439–442, 1996). The isolation and properties of VEGF have been reviewed; see Ferrara et al., *J. Cellular Biochem.,* 47: 211–218, 1991 and Connolly, *J. Cellular Biochem.,* 47: 219–223, 1991.

In addition VEGF has strong chemoattractant activity towards monocytes, can induce the plasminogen activator and the plasminogen activator inhibitor in endothelial cells, and can also induce microvascular permeability. Because of the latter activity, it is sometimes referred to as vascular permeability factor (VPF). VEGF is also chemotactic for certain hematopoetic cells. Recent literature indicates that VEGF blocks maturation of dendritic cells and thereby reduces the effectiveness of the immune response to tumors (many tumors secrete VEGF) (Gabrilovich et al., Blood 92: 4150–4166, 1998; Gabrilovich et al., Clinical Cancer Research 5: 2963–2970, 1999).

Vascular endothelial growth factor B (VEGF-B) is very strongly expressed in heart and only weakly in lung, whereas the reverse is the case for VEGF. Reverse transcriptase-polymerase chain reaction (RT-PCR) assays have demonstrated the presence of VEGF-B mRNA in melanoma, normal skin, and muscle. This suggests that VEGF and VEGF-B, despite the fact that they are co-expressed in many tissues, have functional differences. Gene targeting studies have shown that VEGF-B deficiency results in mild cardiac phenotype, and impaired coronary vasculature (Bellomo et al., Circ. Res. 86:E29–35, 2000).

Human VEGF-B was isolated using a yeast co-hybrid interaction trap screening technique by screening for cellular proteins which might interact with cellular retinoic acid-binding protein type I (CRABP-I). The isolation and characteristics including nucleotide and amino acid sequences for both the human and mouse VEGF-B are described in detail in PCT/US96/02957, and in U.S. Pat. Nos. 5,840,693 and 5,607,918 by Ludwig Institute for Cancer Research and The University of Helsinki and in Olofsson et al., Proc. Natl. Acad. Sci. USA, 93: 2576–2581, 1996.

VEGF-C was isolated from conditioned media of the PC-3 prostate adenocarcinoma cell line (CRL1435) by screening for ability of the medium to produce tyrosine phosphorylation of the endothelial cell-specific receptor tyrosine kinase VEGFR-3 (Flt4), using cells transfected to express VEGFR-3. VEGF-C was purified using affinity chromatography with recombinant VEGFR-3, and was cloned from a PC-3 cDNA library. Its isolation and characteristics are described in detail in Joukov et al., EMBO J., 15: 290–298, 1996.

VEGF-D was isolated from a human breast cDNA library, commercially available from Clontech, by screening with an expressed sequence tag obtained from a human cDNA library designated "Soares Breast 3NbHBst" as a hybridization probe (Achen et al., Proc. Natl. Acad. Sci. USA, 95: 548–553, 1938). Its isolation and characteristics are described in detail in International Patent Application No. PCT/US97/14696 (WO98/07832)

In PCT/US97/14696, the isolation of a biologically active fragment of VEGF-D, designated VEGF-DΔNΔC, is also described. This fragment consists of VEGF-D amino acid residues 93 to 201 linked to the affinity tag peptide FLAG®. The entire disclosure of the International Patent Application PCT/US97/14696 (WO 98/07832) is incorporated herein by reference.

The VEGF-D gene is broadly expressed in the adult human, but is certainly not ubiquitously expressed. VEGF-D is strongly expressed in heart, lung and skeletal muscle. Intermediate levels of VEGF-D are expressed in spleen, ovary, small intestine and colon, and a lower expression occurs in kidney, pancreas, thymus, prostate and testis. No VEGF-D mRNA was detected in RNA from brain, placenta, liver or peripheral blood leukocytes.

PlGF was isolated from a term placenta cDNA library. Its isolation and characteristics are described in detail in Maglione et al., Proc. Natl. Acad. Sci. USA, 88: 9267–9271, 1991. Presently its biological function is not well understood.

VEGF3 was isolated from a cDNA library derived from colon tissue. VEGF3 is stated to have about 36% identity and 66% similarity to VEGF. The method of isolation of the gene encoding VEGF3 is unclear and no characterization of the biological activity is disclosed.

Similarity between two proteins is determined by comparing the amino acid sequence and conserved amino acid substitutions of one of the proteins to the sequence of the second protein, whereas identity is determined without including the conserved amino acid substitutions.

A major function of the lymphatic system is to provide fluid return from tissues and to transport many extravascular substances back to the blood. In addition, during the process of maturation, lymphocytes leave the blood, migrate through lymphoid organs and other tissues, enter the lymphatic vessels, and return to the blood through the thoracic duct. Specialized venules, high endothelial venules (HEVs), bind lymphocytes again and cause their extravasation into tissues. The lymphatic vessels, and especially the lymph nodes, thus play an important role in immunology and in the development of metastasis of different tumors. Unlike blood vessels, the embryonic origin of the lymphatic system is not clear, and at least three different theories exist as to its origin. Lymphatic vessels are difficult to identify due to the absence of known specific markers available for them.

Lymphatic vessels are most commonly studied with the aid of lymphography. In lymphography, X-ray contrast medium is injected directly into a lymphatic vessel. The contrast medium gets distributed along the efferent drainage vessels of the lymphatic system and is collected in the lymph nodes. The contrast medium can stay for up to half a year in the lymph nodes, during which time X-ray analyses allow the follow-up of lymph node size and architecture. This diagnostic technique is especially important in cancer patients with metastases in the lymph nodes and in lymphatic malignancies, such as lymphoma. However, improved materials and methods for imaging lymphatic tissues are needed in the art.

As noted above, the PDGF/VEGF family members act primarily by binding to receptor tyrosine kinases. In general, receptor tyrosine kinases are glycoproteins which comprise an extracellular domain capable of binding a specific growth factor(s), a transmembrane domain, which is usually an alpha-helical portion of the protein, a juxtamembrane domain, which is where the receptor may be regulated by, e.g., protein phosphorylation, a tyrosine kinase domain, which is the enzymatic component of the receptor, and a carboxy-terminal tail, which in many receptors is involved in recognition and binding of the substrates for the tyrosine kinase.

Five endothelial cell-specific receptor tyrosine kinases have been identified, belonging to two distinct subclasses: three vascular endothelial cell growth factor receptors, VEGFR-1 (Flt-1), VEGFR-2 (KDR/Flk-1), VEGFR-3 (Flt4), and the two receptors of the Tie family, Tie and Tie-2 (Tek). These receptors differ in their specificity and affinity. All of these have the intrinsic tyrosine kinase activity which is necessary for signal transduction.

The only receptor tyrosine kinases known to bind VEGFs are VEGFR-1, VEGFR-2 and VEGFR-3. VEGFR-1 and VEGFR-2 bind VEGF with high affinity, and VEGFR-1 also binds VEGF-B and PlGF. VEGF-C has been shown to be the ligand for VEGFR-3, and it also activates VEGFR-2

(Joukov et al., *The EMBO Journal*, 15: 290–298, 1996). VEGF-D binds to both VEGFR-2 and VEGFR-3. A ligand for Tek/Tie-2 has been described in International Patent Application No. PCT/US95/12935 (WO 96/11269) by Regeneron Pharmaceuticals, Inc. The ligand for Tie has not yet been identified.

Recently, a novel 130–135 kDa VEGF isoform specific receptor has been purified and cloned (Soker et al., *Cell*, 92: 735–745, 1998). The VEGF receptor was found to specifically bind the $VEGF_{165}$ isoform via the exon 7 encoded sequence, which shows weak affinity for heparin (Soker et al., *Cell*, 92: 735-745, 1998). surprisingly, the receptor was shown to be identical to human neuropilin-1 (NP-1), a receptor involved in early stage neuromorphogenesis. PlGF-2 also appears to interact with NP-1 (Migdal et al., *J. Biol. Chem.*, 273: 22272–22278, 1998).

VEGFR-1, VEGFR-2 and VEGFR-3 are expressed differently by endothelial cells. Generally, both VEGFR-1 and VEGFR-2 are expressed in blood vessel endothelia (Oelrichs et al., *Oncogene*, 8: 11–18, 1992; Kaipainen et al., *J. Exp. Med.*, 178: 2077–2088, 1993; Dumont et al., *Dev. Dyn.*, 203: 80–92, 1995; Fong et al., *Dev. Dyn.*, 207: 1–10, 1996), and VEGFR-3 is mostly expressed in the lymphatic endothelium of adult tissues (Kaipainen et al., *Proc. Natl. Acad. Sci. USA*, 9: 3566–3570, 1995). VEGFR-3 is also expressed in the blood vasculature surrounding tumors.

Although VEGFR-1 is mainly expressed in endothelial cells during development, it can also be found in hematopoetic precursor cells during early stages of embryogenesis (Fong et al., *Nature*, 376: 66–70, 1995). In adults, monocytes and macrophages also express this receptor (Barleon et al., *Blood*, 87: 3336–3343, 1995). In embryos, VEGFR-1 is expressed by most, if not all, vessels (Breier et al., *Dev. Dyn.*, 204: 228–239, 1995; Fong et al., *Dev. Dyn.*, 207: 1–10, 1996).

The receptor VEGFR-3 is widely expressed on endothelial cells during early embryonic development, but as embryogenesis proceeds becomes restricted to venous endothelium and then to the lymphatic endothelium (Kaipainen et al., *Cancer Res.*, 54: 6571–6577, 1994; Kaipainen et al., *Proc. Natl. Acad. Sci. USA*, 92: 3566–3570, 1995). VEGFR-3 is expressed on lymphatic endothelial cells in adult tissues. This receptor is essential for vascular development during embryogenesis.

The essential, specific role in vasculogenesis, angiogenesis and/or lymphangiogenesis of VEGFR-1, VEGFR-2, VEGFR-3, Tie and Tek/Tie-2 has been demonstrated by targeted mutations inactivating these receptors in mouse embryos. Disruption of the VEGFR genes results in aberrant development of the vasculature leading to embryonic lethality around midgestation.

Analysis of embryos carrying a completely inactivated VEGFR-1 gene suggests that this receptor is required for functional organization of the endothelium (Fong et al., *Nature*, 376: 66–70, 1995). However, deletion of the intracellular tyrosine kinase domain of VEGFR-1 generates viable mice with a normal vasculature (Hiratsuka et al., *Proc. Natl. Acad. Sci. USA*, 95: 9349–9354, 1998). The reasons underlying these differences remain to be explained but suggest that receptor signalling via the tyrosine kinase is not required for the proper function of VEGFR-1.

Analysis of homozygous mice with inactivated alleles of VEGFR-2 suggests that this receptor is required for endothelial cell proliferation, hematopoesis and vasculogenesis (Shalaby et al., *Nature*, 376: 62–66, 1995; Shalaby et al., *Cell*, 89: 981–990, 1997).

Targeted inactivation of both copies of the VEGFR-3 gene in mice resulted in defective blood vessel formation characterized by abnormally organized large vessels with defective lumens, leading to fluid accumulation in the pericardial cavity and cardiovascular failure at post-coital day 9.5 (Dumont et al., *Science*, 282: 946–949, 1998). On the basis of these findings, it has been proposed that VEGFR-3 is required for the maturation of primary vascular networks into larger blood vessels. However, the role of VEGFR-3 in the development of the lymphatic vasculature could not be studied in these mice because the embryos died before the lymphatic system emerged. Nevertheless it is assumed that VEGFR-3 plays a role in development of the lymphatic vasculature and lymphangiogenesis given its specific expression in lymphatic endothelial cells during embryogenesis and adult life. This is supported by the finding that ectopic expression of VEGF-C, a ligand for VEGFR-3, in the skin of transgenic mice, resulted in lymphatic endothelial cell proliferation and vessel enlargement in the dermis. Furthermore this suggests that VEGF-C may have a primary function in lymphatic endothelium, and a secondary function in angiogenesis and permeability regulation which is shared with VEGF (Joukov et al., *EMBO J.*, 15: 290–298, 1996).

In addition, VEGF-like proteins have been identified which are encoded by four different strains of the orf virus. This is the first virus reported to encode a VEGF-like protein. The first two strains are NZ2 and NZ7, and are described in Lyttle et al., *J. Virol.*, 68: 84–92, 1994. A third is D1701 and is described in Meyer et al., *EMBO J.*, 18: 363–374, 1999. The fourth strain is NZ10 and is described in International Patent Application PCT/US99/25869. It was shown that these viral VEGF-like proteins bind to VEGFR-2 on the endothelium of the host (sheep/goat/human) (Meyer et al., *EMBO J.*, 18: 363–374, 1999; and Ogawa et al. *J. Biol. Chem.*, 273: 31273–31282, 1988) and this binding is important for development of infection (International Patent Application PCT/US99/25869). The entire disclosure of the International Patent Application PCT/US99/25869 is incorporated herein by reference. These proteins show amino acid sequence similarity to VEGF and to each other.

The orf virus is a type of species of the parapoxvirus genus which causes a highly contagious pustular dermatitis in sheep and goats and is readily transmittable to humans. The pustular dermatitis induced by orf virus infection is characterized by dilation of blood vessels, swelling of the local area and marked proliferation of endothelial cells lining the blood vessels. These features are seen in all species infected by orf and can result in the formation of a tumor-like growth or nodule due to viral replication in epidermal cells. Generally orf virus infections resolve in a few weeks, but severe infections that fail to resolve without surgical intervention are seen in immune impaired individuals.

The biological functions of the different members of the VEGF family are currently being elucidated. Of particular interest are the properties of VEGF-D and VEGF-C. These proteins bind to both VEGFR-2 and VEGFR-3—localized on vascular and lymphatic endothelial cells respectively— and are closely related in primary structure (48% amino acid identity) Both factors are mitogenic for endothelial cells in vitro.

VEGF-C has been shown to be angiogenic in the mouse cornea model and in the avian chorioallantoic membrane (Cao et al., *Proc. Natl. Acad. Sci. USA* 95: 14389–14394, 1998) and was able to induce angiogenesis in the setting of tissue ischemia (Witzenbichler et al., *Am. J. Pathol.* 153:

381–394, 1998). Furthermore, VEGF-C stimulated lymphangiogenesis in the avian chorioallantoic membrane (Oh et al. , Dev. Biol. 188: 96–109, 1997) and in a transgenic mouse model (Jeltsch et al., Science 276: 1423–1425, 1997).

VEGF-D was shown to be angiogenic in the rabbit cornea (Marconcini et al., Proc. Natl. Acad. Sci. USA 96: 9671–9676, 1999) The lymphangiogenic capacity of VEGF-D has not yet been reported, however, given that VEGF-D, like VEGF-C, binds and activates VEGFR-3, a receptor thought to signal for lymphangiogenesis (Taipale et al. , Curr. Topics Micro. Immunol. 237: 85–96, 1999), it is highly likely that VEGF-D is lymphangiogenic.

VEGF-D and VEGF-C may be of particular importance for the malignancy of tumors, as metastases can spread via either blood vessels or lymphatic vessels; therefore molecules which stimulate angiogenesis or lymphangiogenesis could contribute toward malignancy. This has already been shown to be the case for VEGF. It is noteworthy that VEGF-D gene expression is induced by c-Fos, a transcription factor known to be important for malignancy (Orlandini et al., Proc. Natl. Acad. Sci. USA 93: 11675–11680, 1996). It has been speculated that the mechanism by which c-Fos contributes to malignancy is the up-regulation of genes encoding angiogenic factors.

Each monomer of the VEGF dimer resembles other cystine-knot proteins, having an elongated structure consisting of pairs of twisted, anti-parallel β-strands connected by a series of solvent-exposed loops. The crystal structure of the complex between VEGF and the immunoglobulin-like domain 2 of VEGFR-1 (Wiesmann et al., Cell 91: 695–704, 1997) and mutational analyses (Muller et al., Proc. Natl. Acad. Sci. USA 94: 7192–7197, 1997; Keyt et al., J. Biol. Chem. 271: 5638–5646, 1996) of VEGF indicate that residues important for binding of this molecule to its receptors VEGFR-1 and VEGFR-2 are located primarily on the solvent-exposed loops at the ends of each monomer. The VEGF monomers associate to form disulfide-linked dimers in a side-by-side, head-to-tail fashion, thus creating two symmetrical clusters of receptor binding residues, one at each "pole" of the VEGF dimer.

There is great interest in the development of pharmacological agents which antagonize the receptor-mediated actions of VEGFs (Martiny-Baron and Marme, Curr. Opin. Biotechnol. 6: 675–680, 1995). Monoclonal antibodies to VEGF have been shown to suppress tumor growth in vivo by inhibiting tumor-associated angiogenesis (Kim et al., Nature 362: 841–844, 1993). Similar inhibitory effects on tumor growth have been observed in model systems resulting from expression of either antisense RNA for VEGF (Saleh et al., Cancer Res. 56: 393–401, 1996) or a dominant-negative VEGFR-2 mutant (Millauer et al., Nature 367: 576–579, 1994). While indicating the potential of interfering with the VEGF signalling system as a chemotherapeutic approach, these approaches—being protein- and DNA-based—are not optimal given current pharmaceutical delivery technologies. The development of small molecule antagonists of members of the VEGF family would offer distinct advantages over protein- and DNA-based strategies in terms of oral absorption, penetration across cell membranes, bioavailabilty and biological half life.

SUMMARY OF THE INVENTION

This invention relates to purified monomeric monocyclic peptide inhibitors and purified dimeric bicyclic peptide inhibitors, both based on the peptide sequences of exposed loops of growth factor proteins, such as loops 1, 2 and 3 of VEGF-D, as well as to methods of making them. The invention also relates to pharmaceutical compositions and methods utilizing these peptide inhibitors.

According to one aspect, the invention provides a monomeric monocyclic peptide inhibitor based on loop 1, 2 or 3 of VEGF-D. A preferred peptide interferes with at least the activity of VEGF-D and VEGF-C mediated by VEGF receptor-2 and VEGF receptor-3 (VEGFR-3). A particularly preferred peptide interferes with the activity of VEGF-D, VEGF-C and VEGF mediated by VEGFR-2 and the activity of VEGF-D and VEGF-C mediated by VEGFR-3.

According to another aspect, the invention provides a dimeric bicyclic peptide inhibitor which comprises two monomeric monocyclic peptides, each individually based on loop 1, 2 or 3 of VEGF-D, linked together. A dimeric bicyclic peptide may comprise two monomeric monocyclic peptides which are the same or which are different.

It is also an aspect of the invention to provide a method of making a monomeric monocyclic peptide of the invention. This method comprises synthesizing a linear peptide based on loop 1, 2 or 3 of VEGF-D which includes spaced cysteine residues, oxidizing the linear peptide to a monomeric monocyclic peptide, and optionally purifying the monomeric monocyclic peptide.

An additional aspect provides a method of making a dimeric bicyclic peptide of the invention. This method comprises synthesizing two linear peptides each individually based on loop 1, 2 or 3 of VEGF-D and including appropriately protected, spaced cysteine residues, oxidizing each of the linear peptides to obtain a partially protected monomeric monocyclic peptide, dimerizing the two partially protected momomeric monocyclic peptides to obtain a dimeric bicyclic peptide, and optionally purifying the dimeric bicyclic peptide.

The skilled person is aware that a peptidomimetic compound can be made in which one or more amino acid residues is replaced by its corresponding D-amino acid, substitutions or modifications are made to one or more amino acids in the sequence, peptide bonds can be replaced by a structure more resistant to metabolic degradation and different cyclizing constraints and dimerization groups can be incorporated.

With respect to compounds in which one or more amino acids is replaced by its corresponding D-amino acid, the skilled person is aware that retro-inverso amino acid sequences can be synthesized by standard methods; see, for example, Chorev and Goodman, Acc. Chem. Res., 26: 266–273, 1993.

Olson et al., J. Med. Chem., 36: 3039–3049 1993 provides an example of replacing a peptide bond with a structure more resistant to metabolic degradation.

Peptidomimetic compounds can also be made where individual amino acids are replaced by analogous structures, for example gem-diaminoalkyl groups or alkylmalonyl groups, with or without modified termini or alkyl, acyl or amine substitutions to modify their charge. The use of such alternative structures can provide significantly longer half-life in the body, since they are more resistant to breakdown under physiological conditions.

Methods for combinatorial synthesis of peptide analogs and for screening of peptides and peptide analogs are well known in the art (see, for example, Gallop et al., J. Med. Chem., 37: 1233–1251, 1994). It is particularly contemplated that the compounds of the invention are useful as templates for design and synthesis of compounds of improved activity, stability and bioavailability.

Preferably where amino acid substitution is used, the substitution is conservative, i.e. an amino acid is replaced by one of similar size and with similar charge properties.

As used herein, the term "conservative substitution" denotes the replacement of an amino acid residue by another, biologically similar residue. Examples of conservative substitutions include the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic acid for aspartic acid, or glutamine for asparagine, and the like. Neutral hydrophilic amino acids which can be substituted for one another include asparagine, glutamine, serine and threonine. The term "conservative substitution" also includes the use of a substituted amino acid in place of an unsubstituted parent amino acid.

As such, it should be understood that in the context of the present invention, a conservative substitution is recognized in the art as a substitution of one amino acid for another amino acid that has similar properties. Exemplary conservative substitutions are set out in the following Table A from WO 97/09433.

TABLE A

Conservative Substitutions I

| SIDE CHAIN CHARACTERISTIC | AMINO ACID |
|---|---|
| Aliphatic | |
| Non-polar | G A P |
|  | I L V |
| Polar-uncharged | C S T M |
|  | N Q |
| Polar-charged | D E |
|  | K R |
| Aromatic | H F W Y |
| Other | N Q D E |

Alternatively, conservative amino acids can be grouped as described in Lehninger, [Biochemistry, Second Edition; Worth Publishers, Inc. NY:N.Y. (1975), pp.71–77] as set out in the following Table B.

TABLE B

Conservative Substitutions II

| SIDE CHAIN CHARACTERISTIC | AMINO ACID |
|---|---|
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

Exemplary conservative substitutions are set out in the following Table C.

TABLE C

Conservative Substitutions III

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr, Phe |
| Tyr (Y) | Trp, Phe, Thr, Ser |
| Val (V) | Ile, Leu, Met, Phe, Ala |

If desired, the cyclic peptidomimetic peptides of the invention can be modified, for instance, by glycosylation, amidation, carboxylation, or phosphorylation, or by the creation of acid addition salts, amides, esters, in particular C-terminal esters, and N-acyl derivatives of the peptides of the invention. The peptides also can be modified to create peptide derivatives by forming covalent or noncovalent complexes with other moieties. Covalently-bound complexes can be prepared by linking the chemical moieties to functional groups on the side chains of amino acids comprising the peptides, or at the N- or C-terminus.

In particular, it is anticipated that the aforementioned peptides can be conjugated to a reporter group, including, but not limited to a radiolabel, a fluorescent label, an enzyme (e.g., that catalyzes a calorimetric or fluorometric reaction), a substrate, a solid matrix, or a carrier (e.g., biotin or avidin).

Regarding the cyclizing constraints and dimerization groups, a preferred linking group has 0 to 20 carbon atoms, 0 to 10 heteroatoms (N, O, S, P etc.), straight chain or branched which contain saturated, unsaturated and/or aromatic rings, single and/or double bonds and chemical groups such as amide, ester, disulfide, thioether, ether, phosphate, amine and the like.

The "constraint" used to cyclize the linear peptide can be obtained by several methods, including but not limited to:

(i) cyclizing the N-terminal amine with the C-terminal carboxyl acid function, either directly via an amide bond between the N-terminal nitrogen and C-terminal carbonyl, or indirectly via a spacer group, for example by condensation with an ω-amino carboxylic acid;

(ii) cyclizing via the formation of a covalent bond between the side chains of two residues, such as an amide bond between a lysine residue and either an aspartic acid or glutamic acid residue, or a disulfide bond between two cysteine residues, or a thioether bond between a cysteine residue and an ω-halogenated amino acid residue, either directly or via a spacer group as described in (i) above. The residues contributing the side chains may be derived from the VEGF-D loop sequence itself, or may be incorporated into or added on to the VEGF-D loop sequence for this purpose; and, (iii) cyclizing via the formation of an amide bond between a side chain (for example of a lysine or aspartate residue) and either the C-terminal carboxyl or N-terminal amine, either directly or using a spacer group as described in (i) above. The residues contributing the side chains may be derived from the VEGF-D loop sequence itself, or may be incorporated into or added on to the VEGF-D loop sequence for this purpose.

A still further aspect of the invention makes use of the ability of a peptide of the invention to suppress or interfere with at least one biological activity induced by at least VEGF-D and/or VEGF-C and mediated by VEGF receptor-2 and/or VEGF receptor-3. Examples of such biological activities include vascular permeability, endothelial cell proliferation, angiogenesis, lymphangiogenesis and endothelial cell differentiation. This method comprises administering an effective biological activity interfering amount of a monomeric monocyclic peptide of the invention or a dimeric bicyclic peptide of the invention.

Clinical applications of the invention include, but are not limited to, suppression or inhibition of angiogenesis and/or lymphangiogenesis in the treatment of cancer, diabetic retinopathy, psoriasis and arthropathies. Thus the invention also relates to a method of interfering with angiogenesis, lymphagiogenesis and/or neovascularization in a mammal in need of such treatment which comprises administering an effective amount of a peptide of the invention to the mammal. The peptide interferes with the action of at least VEGF-D and/or VEGF-C by preventing the activation of at least VEGFR-2 and/or VEGFR-3. The cyclic peptide may also interfere with the action of VEGF in the same way as well as the action of VEGF-like proteins from the orf viruses.

This suppression or inhibition of angiogenesis and/or lymphangiogenesis can also occur by targeting a cell expressing VEGFR-2 and/or VEGFR-3 for death. This would involve coupling a toxic compound to a peptide of the invention in order to kill a cell expressing VEGFR-2 and/or VEGFR-3. Such toxic compounds include, but are not limited to, ricin A chain, diphtheria toxin or radionuclides.

As mentioned earlier VEGF blocks maturation of dendritic cells and thereby reduces the effectiveness of the immune response to tumors and VEGF-D and/or VEGF-C may have a similar activity, mediated by VEGFR-2. Therefore inhibitors of VEGF-D/VEGF-C/VEGF should be of use in modulating the immune response to tumors and in other pathological conditions.

Similarly it has been shown that VEGF is chemotactic for certain hematopoetic cells, and VEGF-D and/or VEGF-C may also have similar activity. Thus, inhibition of this process is useful where it is desirable to prevent accumulation of these hematopoetic cells at a specific location or to enhance this process to attract these hematopoetic cells to a specific location.

In addition, this aspect of the invention provides a method of interfering with at least one biological activity selected from angiogenesis, lymphangiogenesis and neovascularization in a disease in a mammal selected from the group of cancer, diabetic retinopathy, psoriasis and arthropathies, comprising the step of administering to said mammal an effective angiogenesis, lymphangiogenesis or neovascularization interfering amount of a peptide of the invention. As noted above, the peptide interferes with the action of at least VEGF-D and VEGF-C by interfering with the activity of VEGF-D and VEGF-C mediated by VEGFR-2 and/or VEGFR-3. The peptide may also interfere with the activity of VEGF mediated by VEGFR-2.

A peptide of the invention can be also be used to modulate vascular permeability in a mammal. Accordingly, the invention provides a method of modulating vascular permeability in a mammal. The method comprises administering to said mammal an effective vascular permeability modulating amount of a monomeric monocyclic peptide of the invention or a dimeric bicyclic peptide of the invention.

A peptide of the invention can be also used to treat conditions, such as congestive heart failure, involving accumulations of fluid in, for example, the lung resulting from increases in vascular permeability, by exerting an offsetting effect on vascular permeability in order to counteract the fluid accumulation. Accordingly, the invention provides a method for treating fluid accumulation in the lung(s), peritoneal cavity, pleura, brain and other body cavities and/or the periphery due to increases in vascular permeability in a mammal. The increase in vascular permeability can also be due to allergic disorders. This method comprises administering to said mammal in need of such treatment an effective vascular permeability decreasing amount of a monomeric monocyclic peptide of the invention or a dimeric bicyclic peptide of the invention.

Another aspect of the invention concerns the provision of a pharmaceutical composition comprising a monomeric mononcyclic peptide of the invention or a dimeric bicyclic peptide of the invention, and a pharmaceutically acceptable non-toxic salt thereof, and a pharmaceutically acceptable solid or liquid carrier or adjuvant. A preferred pharmaceutical composition will inhibit or interfere with a biological activity induced by at least VEGF-D and VEGF-C and mediated by at least VEGFR-2 and/or VEGFR-3. A particularly preferred pharmaceutical composition will inhibit the biological activity induced by VEGF-D, VEGF-C and VEGF and mediated by VEGFR-2 and/or VEGFR-3.

Examples of such a carrier or adjuvant include, but are not limited to, saline, buffered saline, Ringer's solution, mineral oil, talc, corn starch, gelatin, lactose, sucrose, microcrystalline cellulose, kaolin, mannitol, dicalcium phosphate, sodium chloride, alginic acid, dextrose, water, glycerol, ethanol, thickeners, stabilizers, suspending agents and combinations thereof. Such compositions may be in the form of solutions, suspensions, tablets, capsules, creams, salves, elixirs, syrups, wafers, ointments or other conventional forms. The formulation is carried out to suit the mode of administration. Compositions comprising a peptide of the invention will contain from about 0.1% to 90% by weight of the active compound(s), and most generally from about 10% to 30%.

The dose(s) and route of administration will depend upon the nature of the patient and condition to be treated, and will be at the discretion of the attending physician or veterinarian. Suitable routes include oral, subcutaneous, intramuscular, intraperitoneal or intravenous injection, parenteral, topical application, implants etc. For example, an effective amount of a monomeric monocyclic peptide of the invention or a dimeric bicyclic peptide of the invention is administered to an organism in need thereof in a dose between about 0.1 and 1000 µg/kg body weight.

The peptidomimetic peptides of the invention may be used as therapeutic compositions either alone or in combination with other therapeutic agents.

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In the context of the present invention, the peptidomimetic peptides of the present invention may be administered in conjunction with one or more antibodies, antibody conjugates or immune effector cells which target the selected tumor for therapy and that are combined with the immunotherapy and target the vasculature of the tumor to exert a combined therapeutic effect.

Tumor cell resistance to DNA damaging agents represents a major problem in clinical oncology. One goal of current cancer research is to find ways to improve the efficacy of chemo- and radiotherapy. One way is by combining such traditional therapies with gene therapy. For example, the herpes simplex-thymidine kinase (HS-tk) gene, when delivered to brain tumors by a retroviral vector system, successfully induced susceptibility to the antiviral agent ganciclovir (Culver et al., 1992). In the context of the present invention, the peptidomimetic peptides of the present invention may be used similarly in conjunction with chemo- or radiotherapeutic intervention. Peptidomimetic peptide therapy may also be combined with immunotherapy, as described above.

To kill cells, inhibit cell growth, inhibit metastasis, inhibit angiogenesis or otherwise reverse or reduce the malignant phenotype of tumor cells, using the methods and compositions of the present invention, one would generally contact a "target" cell with the therapeutic peptides of the present invention and at least one other agent. These compositions would be provided in a combined amount effective to kill or inhibit proliferation of the cell. This process may involve contacting the cells with the peptidomimetic peptide and the additional agent(s) or factor(s) at the same time. This may be achieved by contacting the cell with a single composition or pharmacological formulation that includes both agents, or by contacting the cell simultaneously with two distinct compositions or formulations, one of which includes the peptidomimetic peptide and the other of which includes the second agent.

Alternatively, the peptidomimetic competitive inhibitor peptide-based therapy treatment may precede or follow the other agent treatment by intervals ranging from minutes to weeks. In embodiments where the other agent and expression construct are applied separately to the cell, it should generally be ensured that a significant period of time does not expire between the time of each delivery, such that the agent and peptidomimetic competitive inhibitor peptide-based therapeutic are still able to exert an advantageously combined effect on the cell. In such instances, it is contemplated that the cell will be contacted with both modalities within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Agents or factors suitable for use in a combined therapy include any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic agents", function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide.

In treating cancer according to the invention, the tumor cells should be contacted with an anti-tumor agent in addition to the peptidomimetic competitive inhibitor peptide-based therapy. This may be achieved by irradiating the localized tumor site with radiation such as X-rays, UV-light, γ-rays or even microwaves. Alternatively, the anti-tumor agent may comprise a therapeutically effective amount of a pharmaceutical compound such as, adriamycin, 5-fluorouracil, etoposide, camptothecin, actinomycin-D, mitomycin C, or cisplatin. The agent may be prepared and used as a combined therapeutic composition, or kit, by combining it with a peptidomimetic inhibitor peptide of the invention, as described above.

Agents that directly cross-link nucleic acids, specifically DNA, are envisaged to facilitate DNA damage leading to a synergistic, antineoplastic combination with peptidomimetic competitive inhibitor peptide-based therapy. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25–75 mg/m$^2$ at 21 day intervals for adriamycin, to 35–50 mg/m$^2$ for etoposide intravenously or double the intravenous dose orally.

Additionally, as mentioned above, the peptidomimetic peptides of the present invention may prove effective in alleviating the symptoms of chronic inflammatory diseases, rheumatoid arthritis, psoriasis and diabetic retinopathy. It is contemplated that the peptides of the instant invention may be combined with traditional anti-inflammatory and other agents that are used in the management of these disorders.

A further aspect of the invention relates to a method for imaging of blood vessels and lymphatic vasculature. This method comprises applying a peptide of the invention to a sample to be imaged; allowing the peptide to bind to a cell surface receptor; and imaging the binding by any suitable means.

The peptide can be directly labeled or indirectly labeled through use of, for example, an antibody to the peptide. The peptide or antibody may be coupled to a suitable supermagnetic, paramagnetic, electron dense, ecogenic or radioactive or non-radioactive agent for imaging. Examples of radioactive agents/labels include a radioactive atom or group, such as $^{125}$I or $^{32}$P. Examples of non-radioactive agents/labels include enzymatic labels, such as horseradish peroxidase or fluorimetric labels, such as fluorescein-5- isothiocyanate (FITC) as well as fluorescent conjugates, such as fluorescent-gold conjugates. Labeling may be direct or indirect, covalent or non-covalent. Images can be obtained from such medical imaging techniques as fluorescence imaging microscopy, magnetic resonance imaging or electron imaging microscopy.

The cyclic monomeric or dimeric peptidomimetic inhibitors of the invention may also be used, for example, to suppress corpus luteum angiogenesis and to treat angiogenesis-related disorders of the female reproductive tract, e.g. endometriosis, ovarian hyperstimulation syndrome, or conditions characterized by ovarian hyperplasia and hypervascularity, such as polycystic ovary syndrome.

DETAILED DESCRIPTION OF PREFERRED EMBODIMENTS

Example 1

Homology Modelling of VEGF-D

A model of the three dimensional (3D) structure of human VEGF-D [amino acids $Val^{101}$—$Pro^{196}$ (SEQ ID NO:1), which correspond to $Lys^{42}$—$Asp^{135}$ of human VEGF (SEQ ID NO:2)] was obtained using protein homology modelling techniques from the known 3D structure of the VEGF dimer. Previously these methods were used to develop a model of the 3D structure of brain-derived neurotrophic factor (BDNF), which was then used successfully in the molecular design of BDNF antagonists (O'Leary and Hughes, *J. Neurochem.* 70: 1712–1721, 1998) and agonists (Australian Provisional Patent Application PQ0848).

Figure 1:
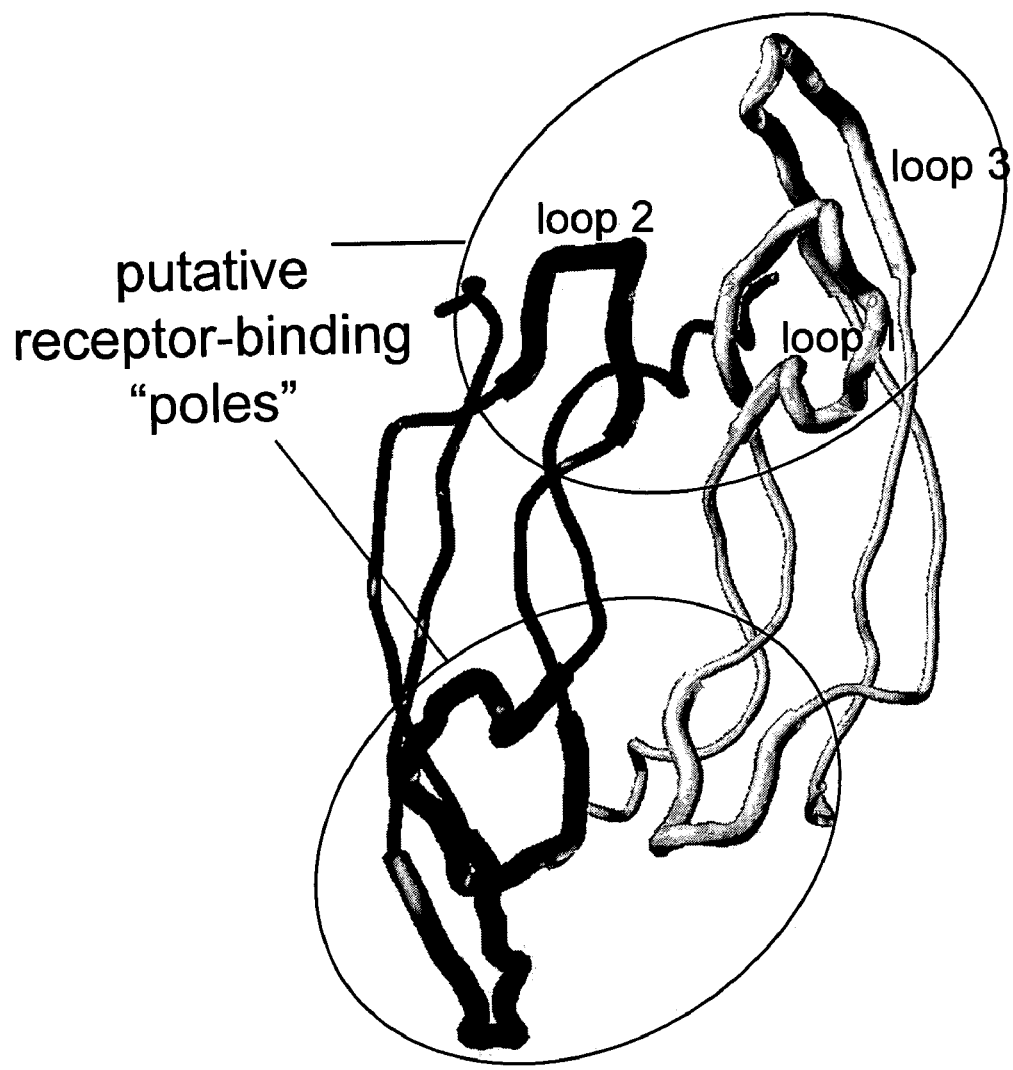
FIG. 1 shows the backbone trace of the three dimensional structure of the VEGF-D dimer showing the positions of the putative receptor binding loops 1, 2 and 3.

Initial homology modelling for VEGF-D was carried out using the Swiss-Model automated protein homology server running at the Glaxo Institute for Molecular Biology in Geneva, Switzerland, accessed via the Internet (See Peitsch, 1995). In the C-terminal 23 amino acid residues of the sequences used for modeling there is low homology between VEGF-D and VEGF. Therefore a theoretical hybrid molecule was generated whose N-terminus consists of amino acids $Val^{101}$—$Thr^{173}$ of VEGF-D (SEQ ID NO:3) and whose C-terminus consists of Gln$^{113}$—Asp$^{135}$ of VEGF$_{165}$ (SEQ ID NO:4). Thus the C-terminal 23 residues of VEGF-D were replaced with the corresponding residues of VEGF. A homology model of this hybrid molecule was then generated using an X-ray crystal structure of the VEGF dimer (Brookhaven Protein Database reference 2VPF) as a template. The resultant model was transferred to the molecular modelling software Sybyl (Tripos Inc. St. Louis, USA), and the C-terminal residues manually mutated to those found in VEGF-D. The VEGF-D diner was then minimized (Sybyl forcefield, Powell conjugate gradient minimization, 1000 cycles) to produce the final VEGF-D diner model, as shown in FIG. 1.

Example 2

Molecular Design of Monomeric Monocyclic Mimetics of Receptor Binding Loops of VEGF-D From the model of VEGF-D described in Example 1, the putative receptor binding loops 1, 2 and 3 were examined in Sybyl for suitable places to insert a molecular constraint to create monomeric monocyclic peptides which mimic the conformation of each of the native loops. To do this, beta beta carbon distances were measured on opposing antiparallel strands in each loop. Beta beta carbon atom distances of less than 6 Å were deemed suitable for the insertion of a disulfide constraint via a cystine residue. Cysteine residues were inserted at these positions and oxidized to form a cystine cyclizing constraint. The resulting monomeric monocyclic peptides were minimized and compared to the corresponding native loop in the VEGF-D dimer model. On the basis of their energy and similarity to the corresponding native loop, the three monomeric monocyclic peptides 1, 2 and 3 based on loops 1, 2 and 3 of VEGF-D were chosen for synthesis.

Example 3

Figure 2:
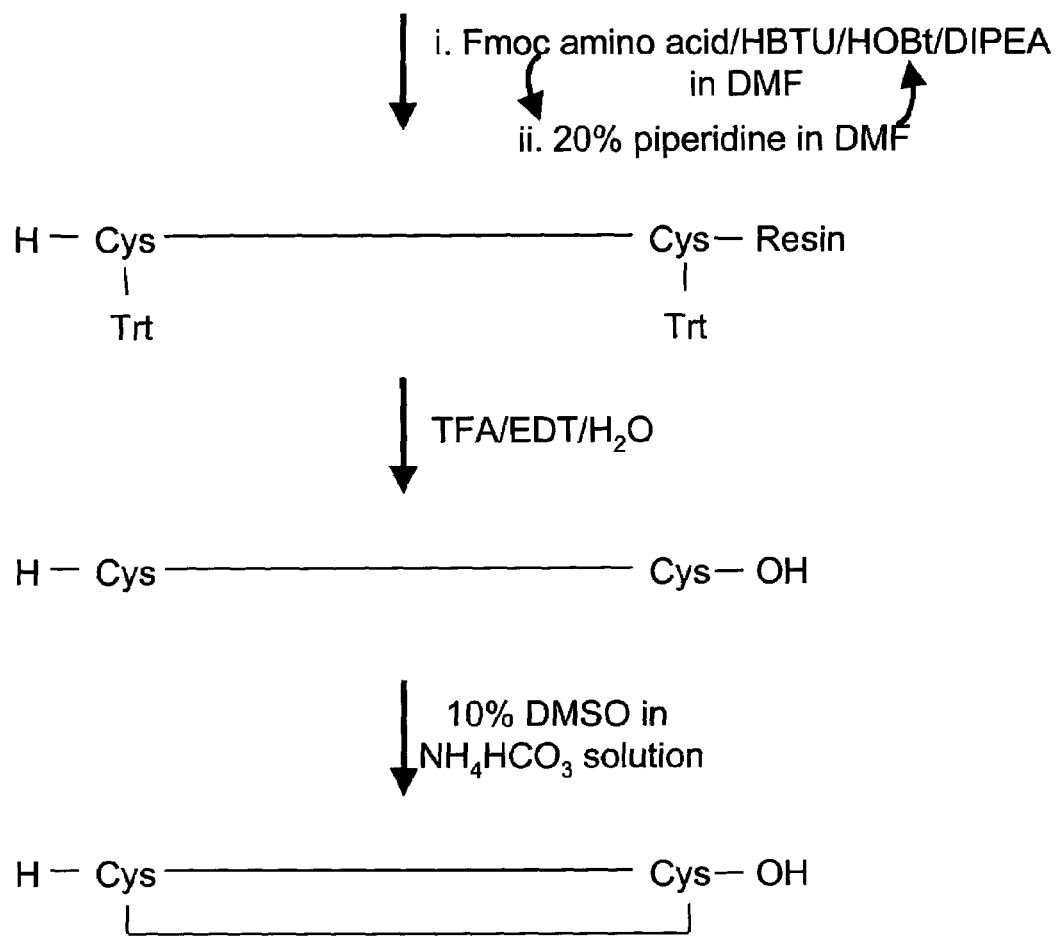
FIG. 2 shows a scheme useful to make monomeric monocyclic peptides according to the invention.

Synthesis of Monomeric Monocyclic Mimetics of Receptor Binding Loops of VEGF-D As illustrated in FIG. 2, the linear peptide precursors to peptides 1, 2 and 3 were assembled from fluorenyl methoxycarbonyl (Fmoc) amino acids manually on chlorotrityl resin (Barlos et al, *Int. J. Peptide Protein Res.* 37: 513–520, 1991) using the batch-type solid phase methods described in Fields and Noble, *Int. J. Peptide Protein Res.* 35: 161–214, 1990. Standard side chain protecting groups were used, including trityl (Trt) protection for the terminal cysteine (Cys) residues. The linear free acids were cleaved from the resin using trifluoracetic acid (TFA)/ethanedithiol (EDT)/H$_2$O (18:1:1). Other abbreviations found in FIG. 2 are:

HBTU: O-benzotriazol-1-yl-N,N,N,N',N'-tetramethyluronium hexafluorophosphate,
HOBT: 1-hydroxybenzotriazole,
DIPEA: diisopropylethanolamine, and
DMF: dimethylformamide.

The crude linear peptides were oxidized to the desired monomeric monocyclic peptides in the presence of 10% dimethylsulfoxide (DMSO) in 0.1M NH$_4$HCO$_3$ solution at pH 8.0 as described in Tam et al., *J. Am. Chem. Soc.* 113: 6657–6662, 1991. The cyclization reactions were monitored by reverse-phase high performance liquid chromatography (RP-HPLC) over a C18 column (Rocket Platinum EPS, Alltech, NSW) using appropriate linear gradients of acetonitrile in 0.1% TFA.

The monomeric monocyclic peptides were purified by RP-HPLC (Econosil C18, Alltech, NSW), and the identity of each peptide confirmed by electrospray mass spectrometry. These peptides are listed in the following Table 1.

TABLE 1

Sequence and predicted and actual molecular masses (determined by mass spectrometry) of peptides synthesized

| number | sequence | mass predicted | mass actual [M + H] |
|---|---|---|---|
| 1 | CASELGKSTNTFC (SEQ ID NO:5) | 1358.52 | 1360 |
| 2 | CNEESLIC (SEQ ID NO:6) | 908.02 | 909.5 |
| 3 | CISVPLTSVPC (SEQ ID NO:7) | 1116.37 | 1117.6 |
| 4 | CASELGKSTNTFCKPPC (SEQ ID NO:8)<br>CASELGKSTNTFCKPPC (SEQ ID NO:8) | 2793.18 | 2793.9 |
| 5 | CASELGKSTNTFCKPPC (SEQ ID NO:8)<br>CCNEESLIC (SEQ ID NO:9) | 3566.09 | 3567.1 |
| 6 | CCNEESLIC (SEQ ID NO:9)<br>CCNEESLIC (SEQ ID NO:9) | 2019.6 | 2020.8 |
| 7 | CSVPLTSVC (SEQ ID NO:10) | 905.41 | 907 |
| 8 | CVPLTSC (SEQ ID NO:11) | 719.32 | 720.5 |
| 9 | CVPLTC (SEQ ID NO:12) | 632.28 | 633.6 |
| 10 | CISVPLSVPC (SEQ ID NO:13) | 1014.5 | 1015.4 |
| 11 | CISVPLVPC (SEQ ID NO:14) | 927.47 | 928.3 |

Example 4

Inhibition of VEGF-D-induced VEGFR-2-mediated Cell Survival by Monomeric Monocyclic Mimetics of Receptor Binding Loops of VEGF-D The purified monomeric monocyclic peptides 1, 2 and 3 were tested for the ability to interfere with the activity of recombinant VEGF-DΔNΔC mediated by mouse VEGFR-2

(also known as Flk 1 and NyK) using the bioassay described in Achen et al., *Proc. Natl. Acad. Sci. USA* 95: 548–553, 1998. The bioassay is also described in Example 7 of International patent application No. PCT/US95/14696 (WO 98/07832). This assay involves the use of Ba/F3 pre-B cells which have been transfected with a plasmid construct encoding a chimeric receptor consisting of the extracellular domain of VEGFR-2 and the cytoplasmic domain of erythropoietin receptor (EpoR) (Ba/F3-NYK-EpoR cells). These cells are routinely passaged in interleukin-3 (IL-3) and will die in the absence of IL-3. However, if signaling is induced from the cytoplasmic domain of the chimeric receptor, these cells survive and proliferate in the absence of IL-3. Such signaling is induced by ligands which bind to the VEGFR-2 extracellular domain of the chimeric receptor. Therefore binding of VEGF-DΔNΔC to the VEGFR-2 extracellular domain causes the cells to survive and proliferate in the absence of IL-3. Addition of monomeric monocyclic peptides which interfere with the binding of such ligands to the extracellular domain or with the activation of the cytoplasmic domain will cause cell death in the absence of IL-3. Parental Ba/F3 cells which lack the chimeric receptor are not induced by VEGF-DΔNΔC to proliferate in the absence of IL-3, indicating that the responses of the Ba/F3-NYK-EpoR cells to these ligands are totally dependent on the chimeric receptor.

Cells were cultured in the presence of IL-3 until required, then washed three times in phosphate buffered saline (PBS), resuspended in IL-3-free cell culture medium (Dulbecco's Modified Eagle's Medium supplemented with fetal calf serum (10%), L-glutamine (1%), geneticin (1 mg/ml), streptomycin (100 μg/ml) and penicillin (60 μg/ml)) and replated in 72-well culture plates (Nunc, Denmark) at a density of approximately 1000 cells/well. Monomeric monocyclic peptides 1, 2 and 3 were added to culture wells to give final concentrations of $10^{-10}$ to $10^{-5}$ M. After incubation for 1 hour at 37° C. in 10% $CO_2$, recombinant VEGF-DΔNΔC (500 ng/ml) was added to the peptide-containing wells at a concentration to produce near-maximal survival. Positive control cultures contained growth factor supernatant alone and negative control cultures contained neither peptide nor growth factor. Cells were grown in culture for 48 hours, after which time a solution of 3-(3,4-dimethylthiazol-2-yl)-2,5-diphenyltetrazoliumbromide (MTT) (500 μg/ml) was added to the cultures, which were incubated for a further 30 minutes. MTT is converted to a blue formazan product by mitochondria, staining living cells blue. Surviving blue cells were counted under a microscope with inverted optics (100×magnification) and cell survival expressed as a percentage of survival in positive control (growth factor only) wells.

Data was analyzed by one way analysis of variance (ANOVA), with a Bonferroni multiple comparisons test carried out post-hoc to test for differences between individual cultures of peptide+ growth factor (treatment) with growth factor alone (positive control).

Figure 3A:
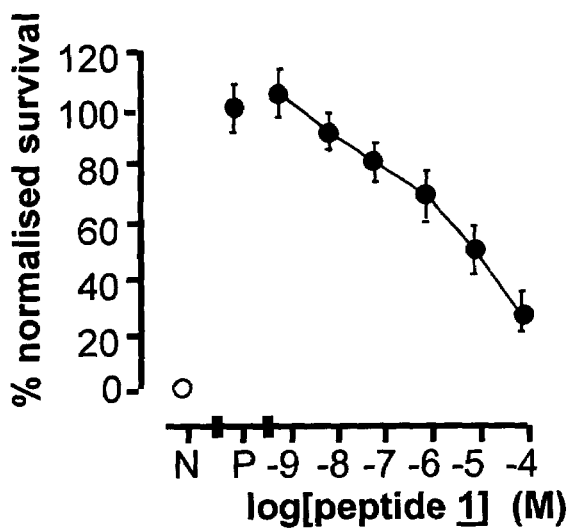
FIGS. 3a–c show the effects of peptide 1 (3a), peptide 2 (3b) and peptide 3 (3c), respectively, on VEGF-D mediated cell survival in the VEGFR-2 bioassay after 48 hours in culture.
Figure 3B:
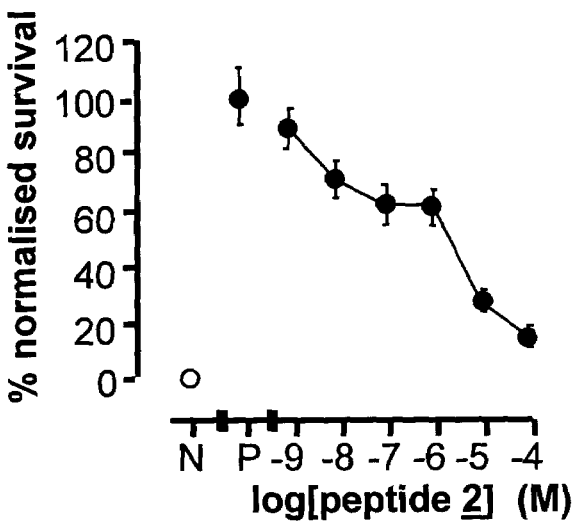
Figure 3C:
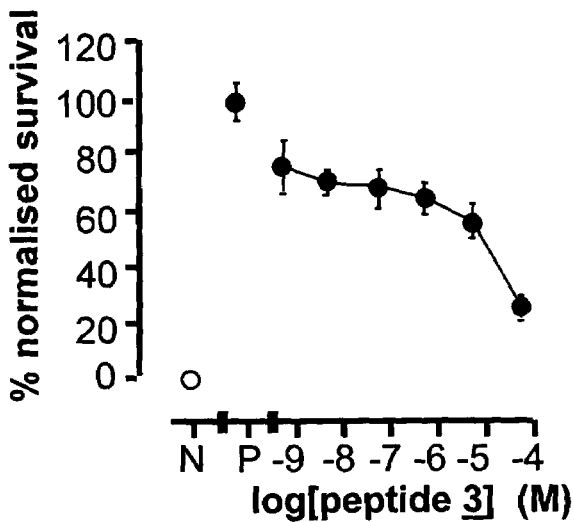

As shown in FIGS. 3a–c, respectively, peptides 1, 2 and 3 were found to inhibit VEGF-D-induced VEGFR-2-mediated cell survival. Although none of the peptides completely inhibited the action of VEGF-DΔNΔC in these assays, they each showed appreciable inhibition at the highest concentration used, $10^{-4}$ M (peptide 1: 79±5%; peptide 2: 86±3%; peptide 3: 74±3%). Cell survival was normalized such that survival in negative controls (N) was set to 0 (typically no viable cells were seen in negative controls), while survival in positive controls (P) was set to 100% (typically 300–400 cells/well).

Example 5

Inhibition of VEGF-induced VEGFR-2-mediated Cell Survival by Monomeric Monocyclic Mimetics of Receptor Binding Loops of VEGF-D Next the monomeric monocyclic peptides 1, 2 and 3 each were assessed for their ability to inhibit the VEGF-induced VEGFR-2-mediated cell survival in the cell-based bioassay described in Example 4. The assay was carried out as described in Example 4, except that the peptides were assayed in competition with recombinant mouse $VEGF_{164}$ (10 ng/ml).

Figure 4A:
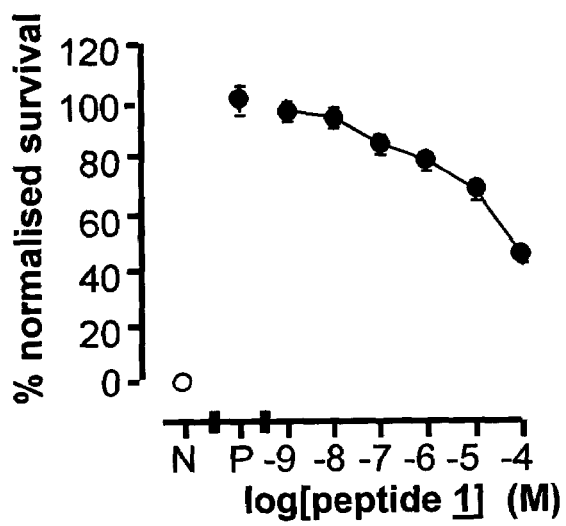
FIGS. 4a–c show the effects of peptide 1 (4a), peptide 2 (4b) and peptide 3 (4c), respectively, on VEGF mediated cell survival in the VEGFR-2 bioassay after 48 hours in culture.
Figure 4B:
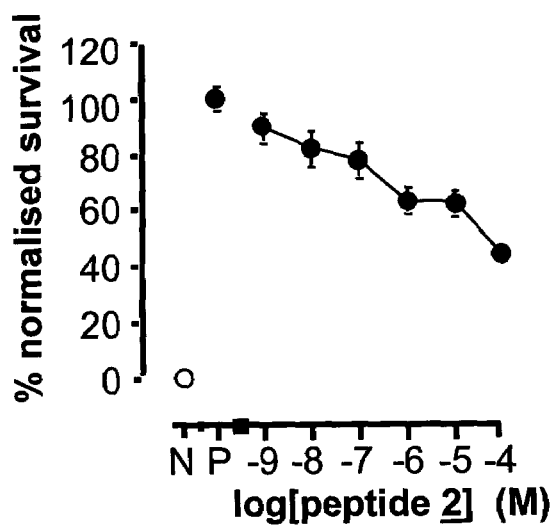
Figure 4C:
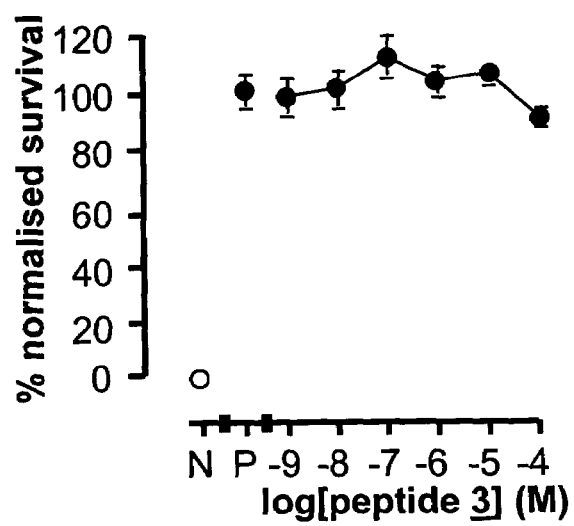

As shown in FIGS. 4a–b, respectively, monomeric, monocyclic peptides 1 and 2, were found to inhibit VEGF-induced VEGFR-2-mediated cell survival in a concentration dependent manner. In these experiments, the maximal inhibitory effect (observed at $10^{-4}$M) of peptides 1 (56±2%) and 2 (56±3%) was less than that observed for the same peptides against VEGF-D. In comparison, the monomeric monocyclic peptide 3 did not inhibit VEGF-induced VEGFR-2-mediated cell survival at any of the concentrations tested (FIG. 4c). This latter result was surprising, in that peptide 3 was an effective inhibitor of VEGF-D-mediated cell survival (see Example 4 above). Cell survival was normalized as above such that survival in negative controls (N, containing neither VEGF nor peptide) was set to 0 (typically no viable cells were seen in negative controls), while survival in positive controls (P, containing VEGF alone) was set to 100% (typically 300–400 cells/well).

Example 6

Figure 5A:
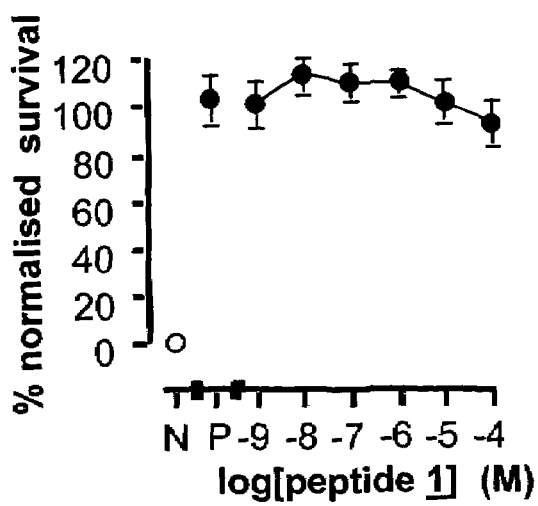
FIGS. 5a–c show the effects of peptide 1 (5a), peptide 2 (5b) and peptide 3 (5c), respectively, on IL-3 mediated cell survival/proliferation in the VEGFR-2 bioassay after 48 hours in culture.
Figure 5B:
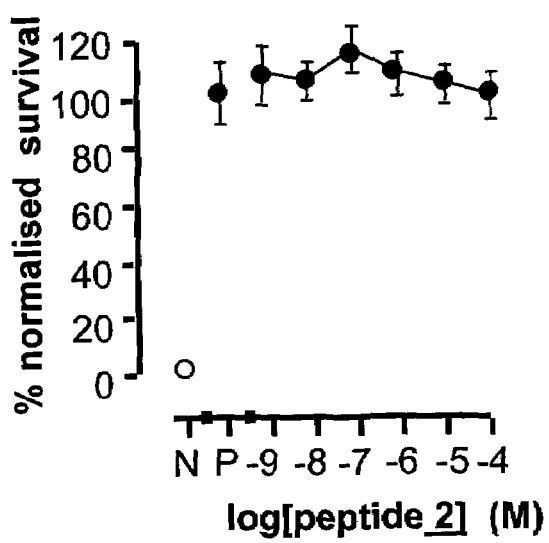
Figure 5C:
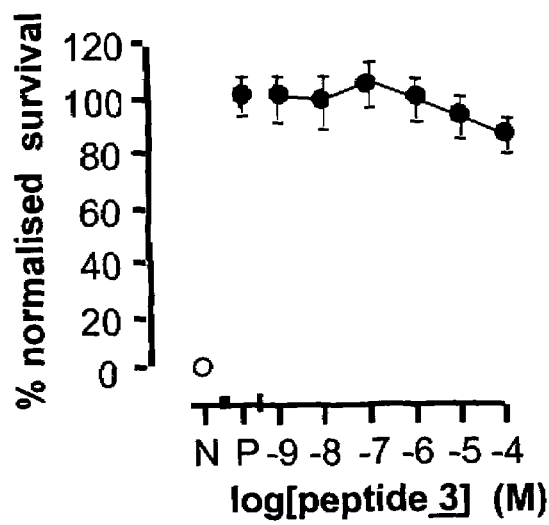

Specificity of Inhibition of VEGFR-2 Ligand Mediated Cell Survival by Monomeric Monocyclic Mimetics of Receptor Binding Loops of VEGF-D To determine the specificity of the monomeric monocyclic peptides 1, 2 and 3, the peptides were assayed in competition with IL-3. The assay was carried out as described in Example 4, except that the peptides were assayed in competition with recombinant IL-3 (10 ng/ml). As shown in FIGS. 5a–5c, respectively, neither peptide 1, 2 nor 3 was found to inhibit the action of IL-3 in this assay. Cell survival was again normalized such that survival in negative controls (N, containing neither IL-3 nor peptide) was set to 0 (typically no viable cells were seen in negative controls), while survival in positive controls (P, containing IL-3 alone) was set to 100% (typically 300–400 cells/well).

Example 7

Figure 6:
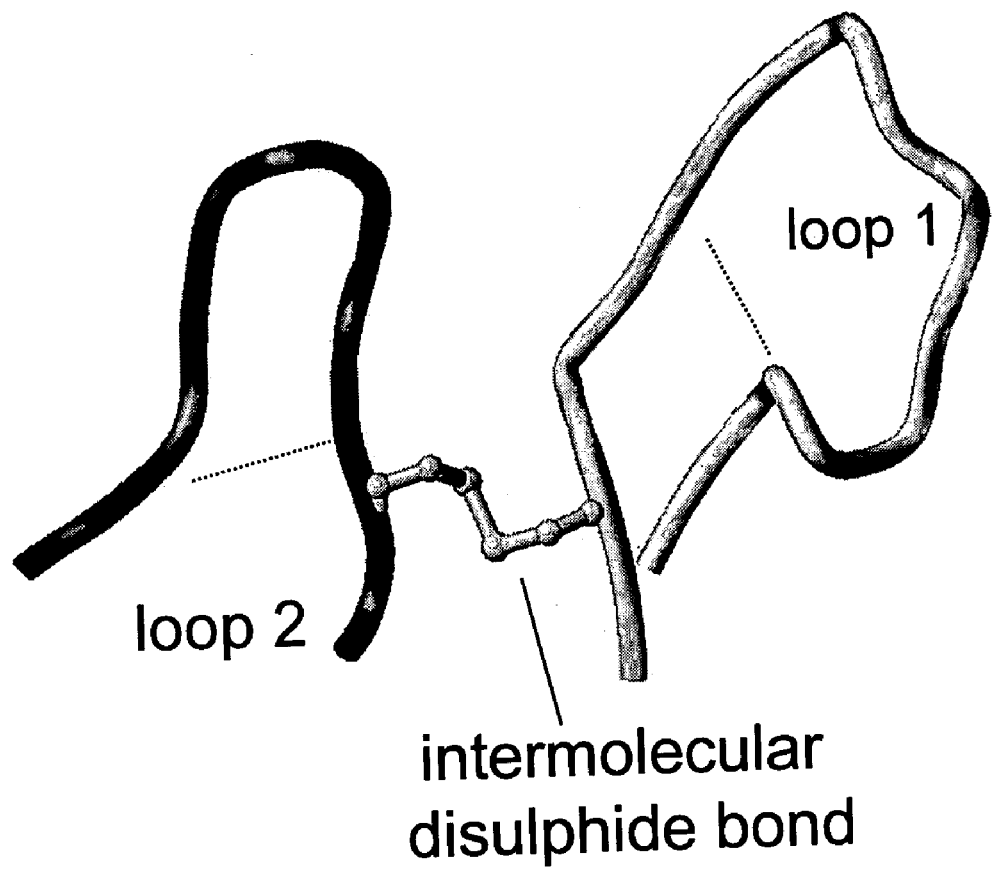
FIG. 6 shows a backbone trace of the predicted three dimensional structure of loop 1 of VEGF-D (contributed by one monomer) and loop 2 of VEGF-D (contributed by the other monomer).

Molecular Design of Bicyclic Dimeric Mimetics of Receptor Binding Loops of VEGF-D Next bicyclic dimeric mimetics were constructed. To aid in the design of such peptides, the same model of VEGF-D was used. Examination of this model showed that loops 1 and 2 are juxtaposed, one loop being contributed by one VEGF-D monomer, the other coming from the other monomer (FIG. 1). As indicated in FIG. 6, these loops are predicted to be connected to one another by an intermolecular disulfide bond between $Cys^{136}$ of loop 1 and $Cys^{145}$ of loop 2. Dotted lines show the approximate positions of the cysteine residues used to constrain the monocyclic monomeric mimetics of loop 1 and loop 2 (peptides 1 and 2 respectively). Using this information, the heterodimeric, bicyclic peptide 5 was designed (Table 1).

Example 8

Synthesis of Bicyclic Dimeric Mimetics of Receptor Binding Loops of VEGF-D

Figure 7:
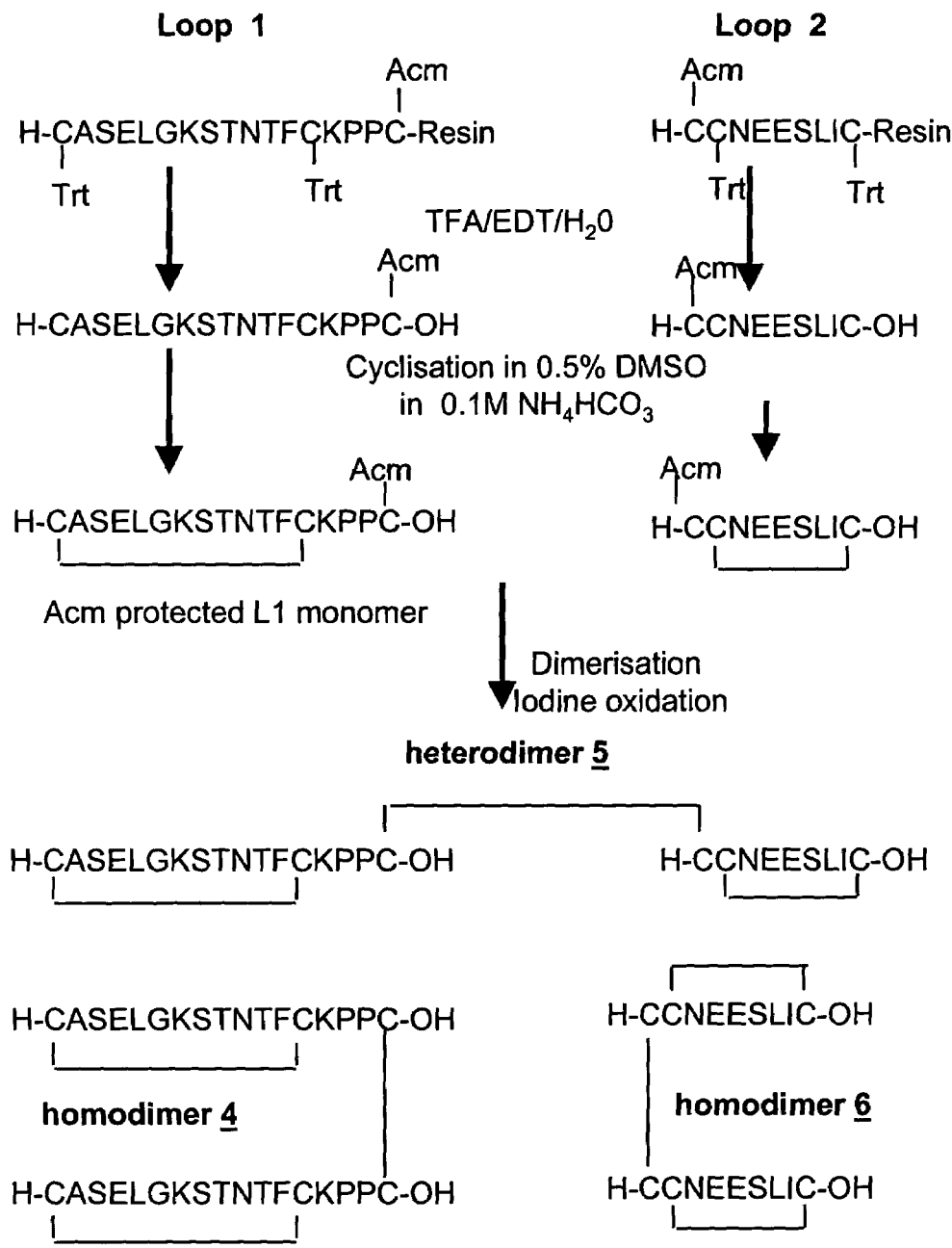
FIG. 7 shows a scheme useful to make dimeric bicyclic peptides according to the invention.

As illustrated in FIG. 7, the heterodimeric bicyclic peptide 5 was synthesized using a mixed cysteine-protection strategy. Briefly, linear L1 and L2 peptides—suitably lengthened to allow formation of a dimerizing linkage analogous to that predicted to exist in native VEGF-D—were assembled from fluorenyl methoxycarbonyl (Fmoc) amino acids and cleaved from the resin as described in Example 3, using TFA-labile Trt protection on the Cys residues to be cyclized, and the TFA-stable acetamidomethyl (Acm) protecting group on the Cys residues to be used to form the dimerization linkage. The linear L1 and L2 peptides were cyclized via their free Cys residues to give the partially-(Acm-) protected monomeric monocyclic peptides. Following their purification by RP-HPLC as described in Example 3, the two partially-protected monomeric monocyclic peptides were dimerized by stirring an equimolar solution of the peptides in the presence of iodine. These conditions should both remove the Acm protecting group and oxidize the resultant free Cys residues to the disulfide-linked cysteine. As shown in FIG. 7, this same approach yielded the homodimers 4 and 6.

Figure 8A:
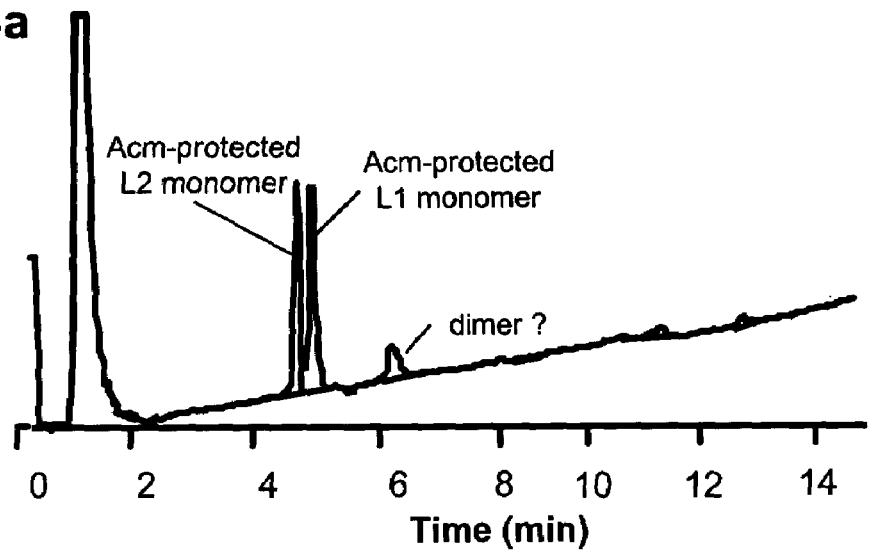
FIGS. 8a–b show an HPLC trace of samples taken from the dimerization reaction of Acm-protected loop 1 and loop 2 monomers two minutes (8a) and three hours (8b), respectively, after commencing the reaction.
Figure 8B:
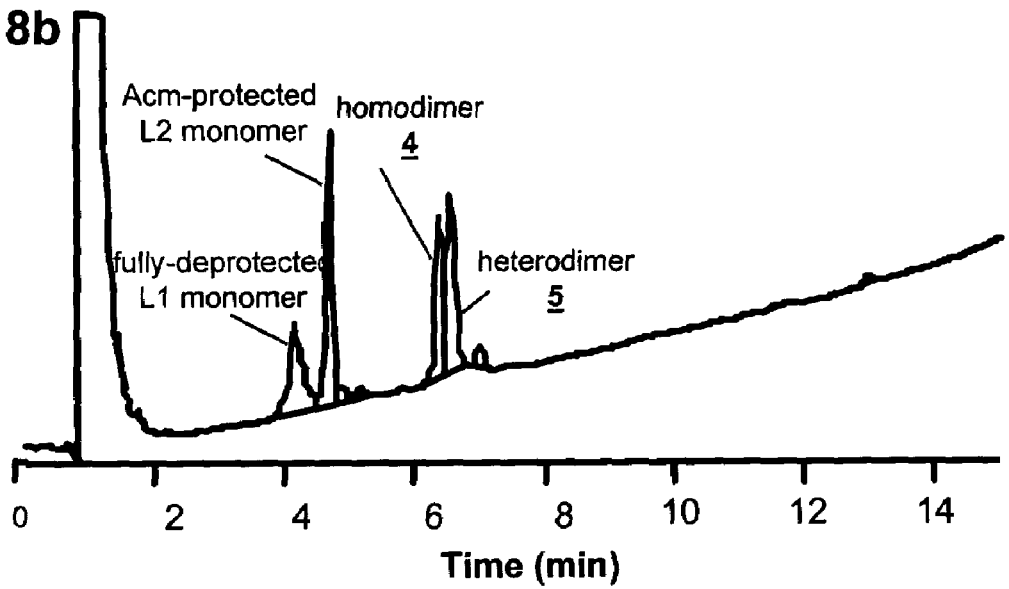

The dimerization reaction was monitored by RP-HPLC, as shown in FIG. 8. After three hours, all of one of the starting compounds (the Acm-protected monomeric monocyclic L1 peptide) had reacted, although there was still some of the other starting compound (the Acm-protected monomeric monocyclic L2 peptide). Also, three new peaks could be detected. Mass spectrometry analysis of these peaks showed them to have molecular weights consistent with fully deprotected monomeric monocyclic peptide L1, the bicyclic homodimer 4 as well as the bicyclic heterodimer 5. No appreciable amounts of either the fully deprotected monomeric monocyclic peptide L2 or the bicyclic homodimer 6 could be detected, indicating that the iodine-mediated removal of Acm from the L2 peptide was significantly slower than the removal of Acm from the L1 peptide. The bicyclic heterodimer 5 and the bicyclic homodimer 4 were purified by RP-HPLC as described in Example 3.

The bicyclic homodimer 6 was synthesized by treating a solution of the partially-protected monomeric monocyclic peptide L2 with iodine. The desired compound was purified by RP-HPLC as described in Example 3.

Example 9

Figure 9A:
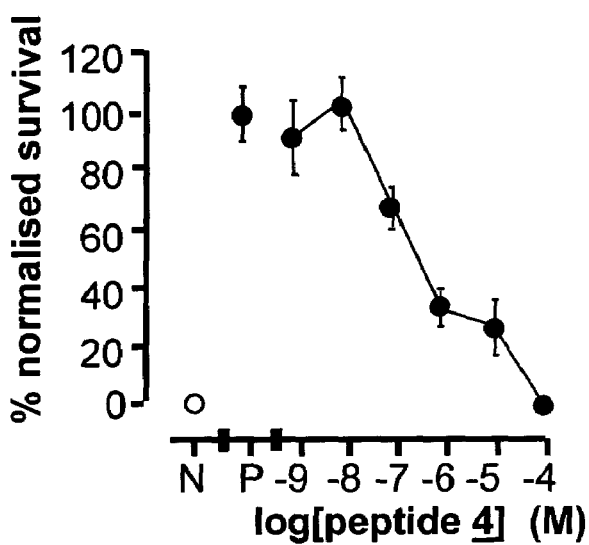
FIGS. 9a–c show the effects of peptide 4 (9a), peptide 5 (9b) and peptide 6 (9c), respectively, on VEGF-D mediated cell survival in the VEGFR-2 bioassay after 48 hours in culture.
Figure 9B:
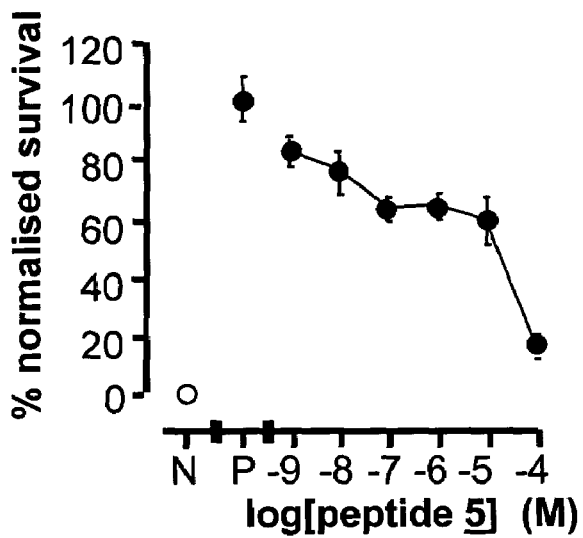
Figure 9C:
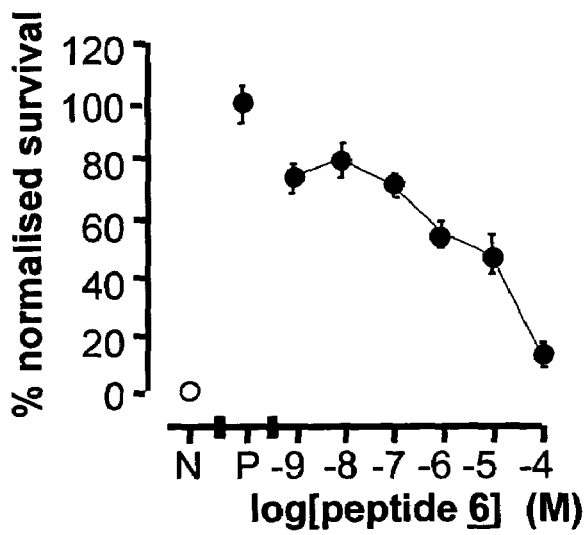

Inhibition of VEGF-D-induced VEGFR-2-mediated Cell Survival by Dimeric Bicyclic Mimetics of Receptor Binding Loops of VEGF-D The heterodimeric bicyclic peptide 5 and the homodimeric bicyclic peptides 4 and 6 each were assayed in competition with VEGF-DΔNΔC in the cell-based bioassay described in Example 4. As shown in FIGS. 9a–c, all three peptides caused a concentration dependent inhibition of VEGF-D-mediated cell survival to a greater extent than any of the monomeric monocyclic peptides 1, 2 or 3 [maximum inhibition (at $10^{-4}$ M) peptide 4: 100% (FIG. 9a); peptide 5: 84±4% (FIG. 9b); peptide 6: 87±4% (FIG. 9c)]. Cell survival was normalized such that survival in negative controls (N, containing neither VEGF-D nor peptide) was set to 0 (typically no viable cells were seen in negative controls), while survival in positive controls (P, containing VEGF-D alone) was set to 100% (typically 300–400 cells/well).

Example 10

Figure 10A:
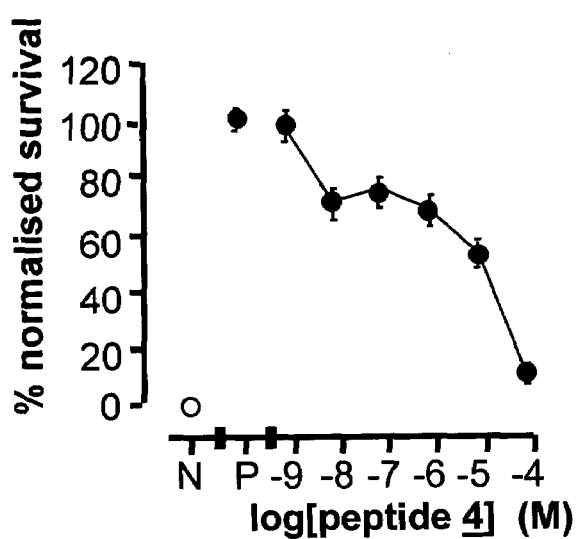
FIGS. 10a–c show the effects of peptide 4 (10a), peptide 5 (10b) and peptide 6 (10c), respectively, on VEGF mediated cell survival in the VEGFR-2 bioassay after 48 hours in culture.
Figure 10B:
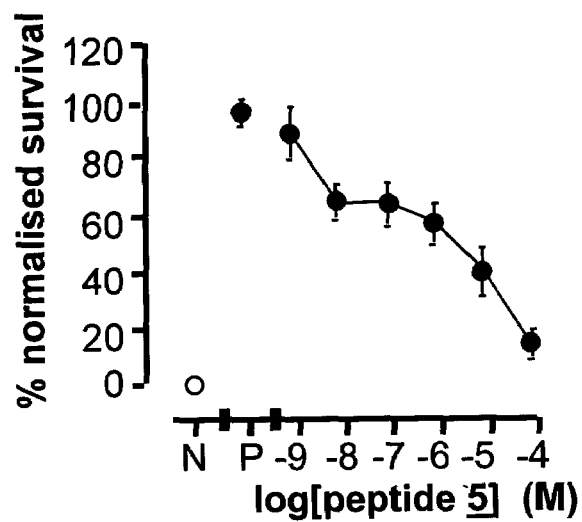
Figure 10C:
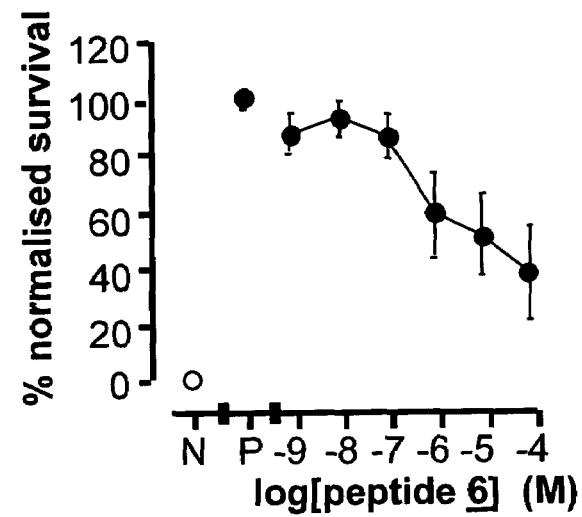

Inhibition of VEGF-induced VEGFR-2-mediated Cell Survival by Dimeric Bicyclic Mimetics of Receptor Binding Loops of VEGF-D Next, the heterodimeric bicyclic peptide 5 and the homodimeric bicyclic peptides 4 and 6 each were subsequently assayed in competition with VEGF in the cell-based bioassay described in Example 4. As shown in Figures 10a–c, all three peptides caused a concentration dependent inhibition of VEGF mediated cell survival again to a greater extent than any of the monomeric monocyclic peptides 1, 2 or 3 [maximum inhibition (at $10^{-4}$ M) peptide 4: 90±2% (FIG. 10a); peptide 5: 87±3% (FIG. 10b); peptide 6: 61±10% (FIG. 10c)]. Cell survival was normalized such that survival in negative controls (N, containing neither VEGF nor peptide) was set to 0 (typically no viable cells were seen in negative controls), while survival in positive controls (P, containing VEGF alone) was set to 100% (typically 300–400 cells/well).

Example 11

Figure 11A:
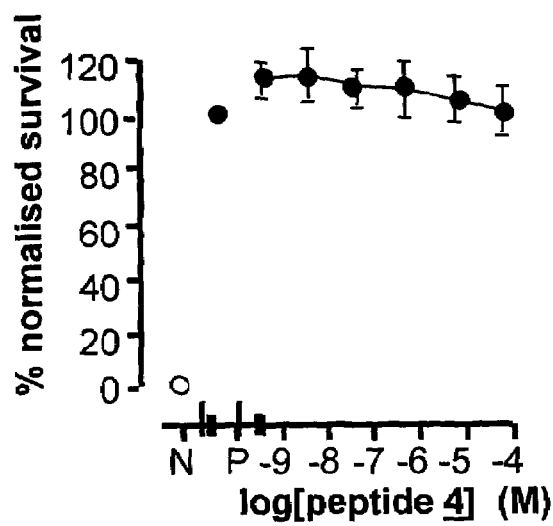
FIGS. 11a–c shows the effects of peptide 4 (11a), peptide 5 (11b) and peptide 6 (11c), respectively, on IL-3 mediated cell survival/proliferation in the VEGFR-2 bioassay after 48 hours in culture.
Figure 11B:
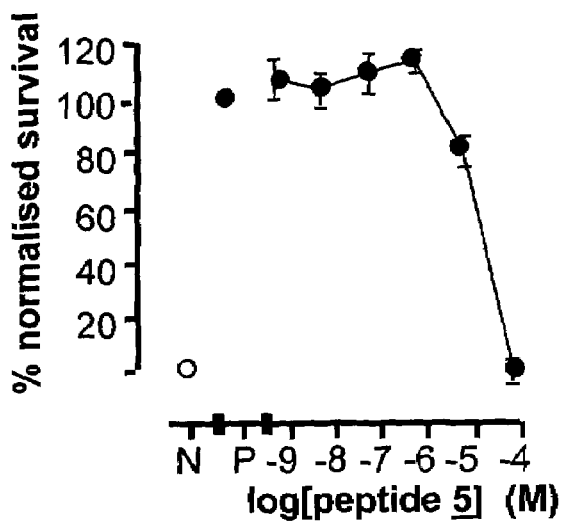
Figure 11C:
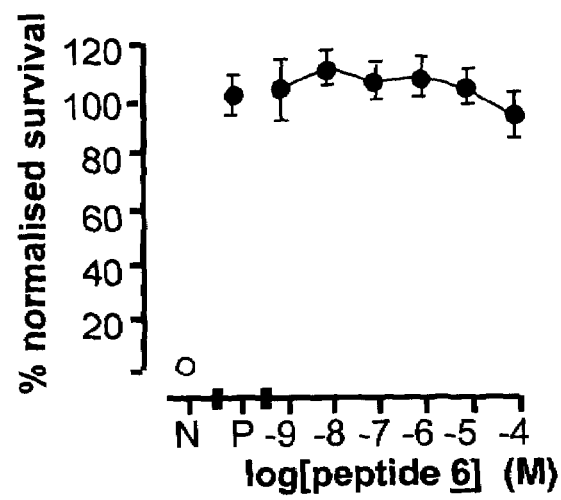

Specificity of Inhibition of VEGFR-2 Ligand Mediated Cell Survival by Dimeric Bicyclic Mimetics of Receptor Binding Loops of VEGF-D When assayed in competition with IL-3, the heterodimeric bicyclic peptide 5 caused a significant reduction in cell number, of 98±2%, at $10^{-4}$ M (FIG. 11b). In contrast neither of the homodimeric bicyclic peptides 4 or 6 caused a significant change in cell number, compared to the IL-3 only controls, as shown in FIGS. 11a and 11c, respectively. Cell survival is normalized such that survival in negative controls (N, containing neither IL-3 nor peptide) was set to 0 (typically no viable cells were seen in negative controls), while survival in positive controls (P, containing IL-3 alone) was set to 100% (typically 300–400 cells/well).

Example 12

Inhibition of VEGF-D-induced VEGFR-3-mediated Cell Survival by Monomeric Monocyclic Mimetics and Dimeric Bicyclic Mimetics of Receptor Binding Loops of VEGF-D The purified monomeric monocyclic peptides 1, 2 and 3 and the dimeric bicyclic peptides 4, 5 and 6 were tested for the ability to interfere with the activity of recombinant VEGF-DΔNΔC mediated by mouse VEGFR-3 using a modification of the bioassay described in Achen et al., *Eur. J. Biochem.*, 267: 2505–2515, 2000. This assay involves the use of Ba/F3 pre-B cells which have been transfected with a plasmid construct encoding a chimeric receptor consisting of the extracellular domain of VEGFR-3 and the cytoplasmic domain of erythropoietin receptor(EpoR). These cells are routinely passaged in the presence of interleukin-3 (IL-3) and will die in the absence of IL-3. However, if signaling is induced from the cytoplasmic domain of the chimeric receptor, these cells survive and proliferate in the absence of IL-3. Such signaling is induced by ligands which bind to the VEGFR-3 extracellular domain of the chimeric receptor.

Therefore binding of VEGF-D to the VEGFR-3 extracellular domain causes the cells to survive and proliferate in the absence of IL-3. Addition of peptides which interfere with the binding of such ligands to the extracellular domain or with the activation of the cytoplasmic domain will cause cell death in the absence of IL-3. Parental Ba/F3 cells which lack the chimeric receptor are not induced by ligands for VEGFR-3 to proliferate in the absence of IL-3, indicating that the responses of the transfected cells to these ligands are totally dependent on the chimeric receptor.

Cells were cultured in the presence of IL-3 until required, then washed three times in phosphate buffered saline (PBS), resuspended in IL-3-free cell culture medium (Dulbecco's Modified Eagle's Medium supplemented with fetal calf serum (10%), L-glutamine (1%), geneticin (1 mg/ml), streptomycin (100 µg/ml) and penicillin (60 µg/ml)) and replated in 72-well culture plates (Nunc, Denmark) at a density of approximately 1000 cells/well. Monomeric monocyclic peptides 1, 2 and 3 and the dimeric bicyclic peptides 4, 5 and 6 were added to culture wells to give final concentrations of $10^{-10}$ to $10^{-5}$ M. After incubation for 1 hour at 37° C. in 10% $CO_2$, recombinant VEGF-DΔNΔC (500 ng/ml) was added to the peptide-containing wells at a concentration to produce near-maximal survival. Positive control cultures contained VEGF-DΔNΔC alone and negative control cultures contained neither peptide nor growth factor. Cells were grown in culture for 48 hours, after which time a solution of 3-(3,4-dimethylthiazol-2-yl)-2,5-diphenyltetrazolium bromide (MTT 500 µg/ml) was added to the cultures, which were incubated for a further 30 minutes. MTT is converted to a blue formazan product by mitochondria, staining living cells blue. Surviving blue cells were counted under a microscope with inverted optics (100×magnification) and cell survival expressed as a percentage of survival in positive control (growth factor only) wells. Cell survival was normalized such that survival in negative controls (N) was set to 0 (typically no viable cells were seen in negative controls), while survival in positive controls (P) was set to 100% (typically 300–400 cells/well). Data was obtained in triplicate from three separate experiments.

Figure 12A:
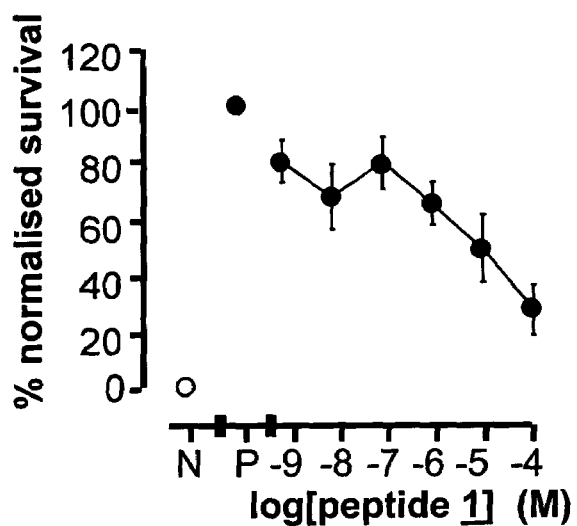
FIGS. 12a–c show the effects of peptide 1 (12a), peptide 2 (12b) and peptide 3 (12c), respectively, on VEGF-D mediated cell survival in the VEGFR-3 bioassay after 48 hours in culture.
Figure 12B:
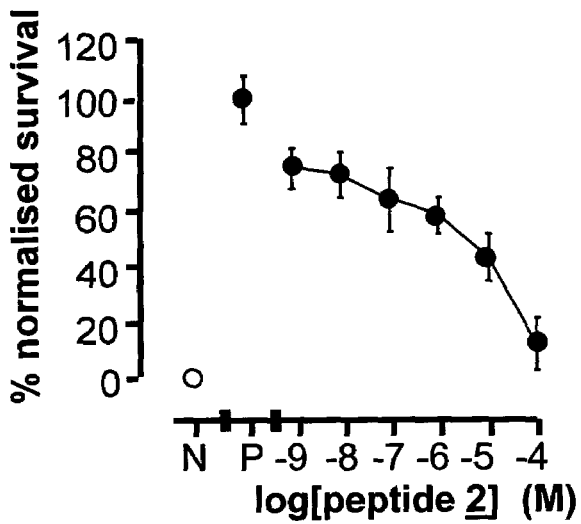
Figure 12C:
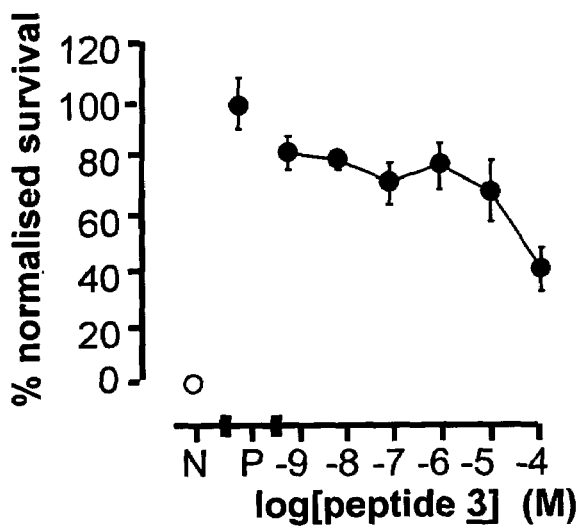
Figure 13A:
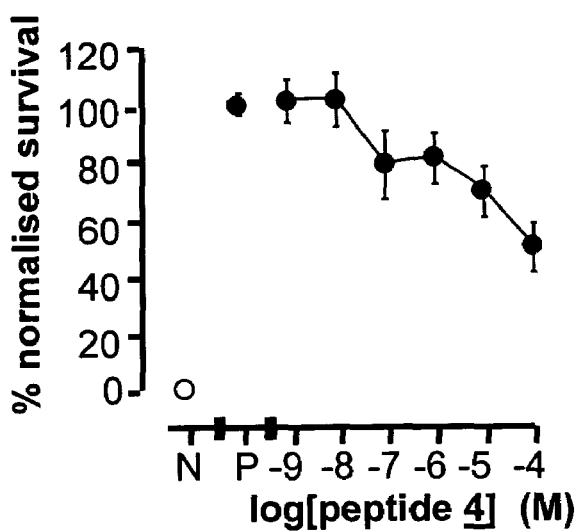
FIGS. 13a–c show the effects of peptide 4 (13a), peptide 5 (13b) and peptide 6 (13c), respectively, on VEGF-D mediated cell survival in the VEGFR-3 bioassay after 48 hours in culture.
Figure 13B:
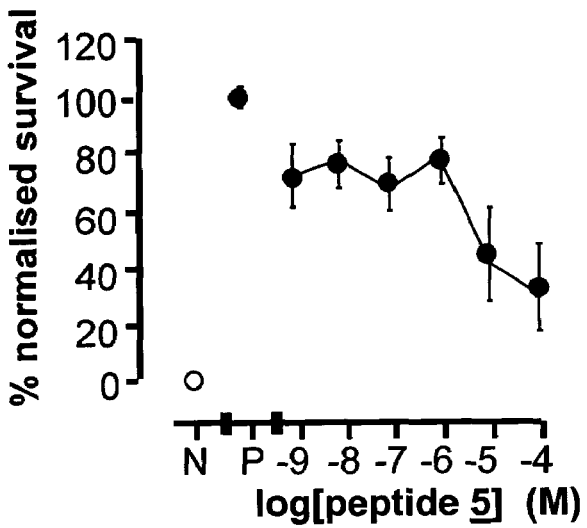
Figure 13C:
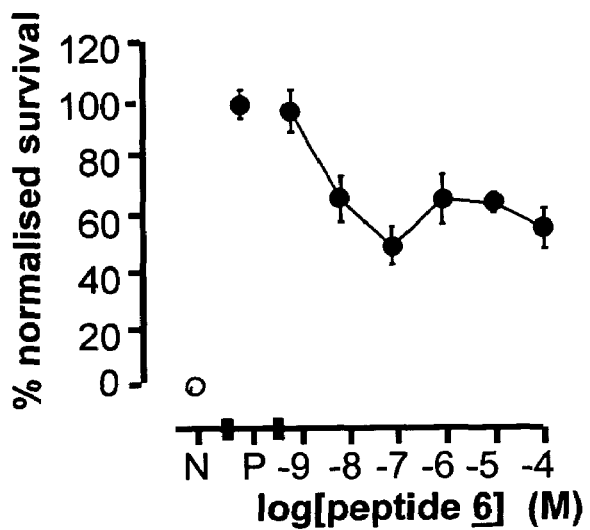

As shown in FIGS. 12a–c, respectively, the monomeric monocyclic peptides 1, 2 and 3 were found to inhibit VEGF-D-induced VEGFR-3-mediated cell survival. Although no peptide completely inhibited survival, all three peptides were effective inhibitors at the highest concentration used, $10^{-4}$ M (peptide 1: 73±9%; peptide 2: 88±10%; peptide 3: 61±8%). Similarly, the dimeric bicyclic peptides 4, 5 and 6 (FIGS. 13a–c, respectively) also inhibited VEGF-D-induced VEGFR-3-mediated cell survival (inhibition at $10^{-4}$ M: peptide 4: 52±9%; peptide 5: 69±16%; peptide 6: 44±7%). These results differ somewhat from those obtained with the inhibition of VEGF-D-induced VEGFR-2-mediated cell survival described in Examples 4 and 9 above, in that none of the dimeric bicyclic peptides appear to be more effective inhibitors than the monomeric monocyclic peptides.

Example 13

Inhibition of VEGF-C-induced VEGFR-2-mediated Cell Survival by Monomeric Monocyclic Mimetics and Dimeric Bicyclic Mimetics of Receptor Binding Loops of VEGF-D The purified monomeric monocyclic peptides 1, 2 and 3 and the dimeric bicyclic peptides 4, 5 and 6 were tested for the ability to interfere with the activity of recombinant VEGF-C mediated by mouse VEGFR-2. Cells were passaged and the assay carried out in an analogous manner to that described in Example 4 above, except that 1 hour after the addition of the monomeric monocyclic peptides 1, 2 and 3 and the dimeric bicyclic peptides 4, 5 and 6 to the respective culture wells, recombinant VEGF-CΔNΔC (the VEGF homology domain of VEGF-C, described previously in Joukov et al., *EMBO J.* 16: 3898–3 1911, 1997) was added, at a concentration to produce near-maximal survival (50 ng/ml).

Figure 14A:
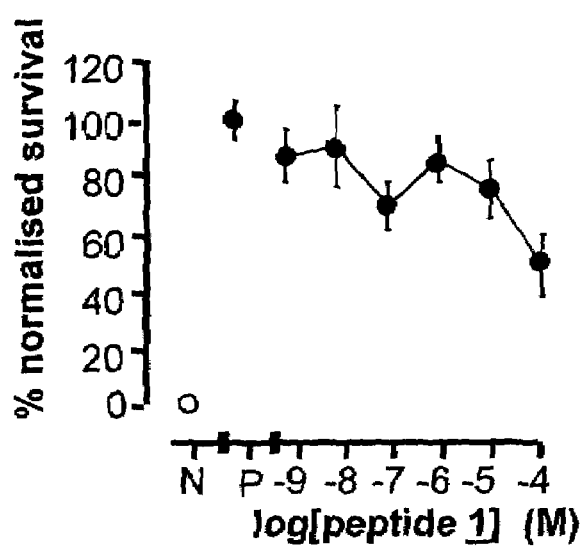
FIGS. 14a–c show the effects of peptide 1 (14a), peptide 2 (14b) and peptide 3 (14c), respectively, on VEGF-C mediated cell survival in the VEGFR-2 bioassay after 48 hours in culture.
Figure 14B:
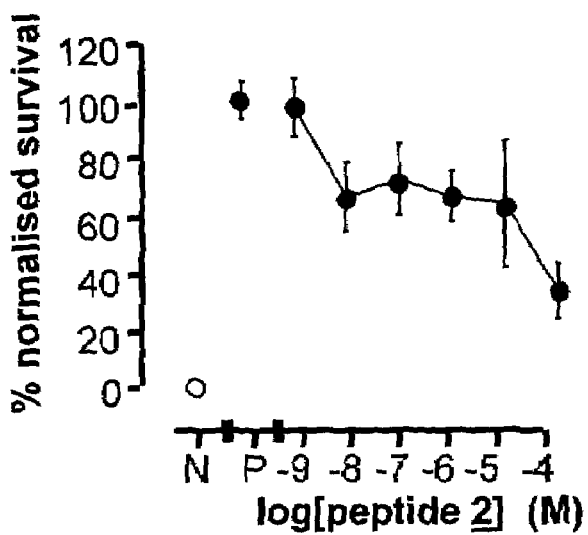
Figure 14C:
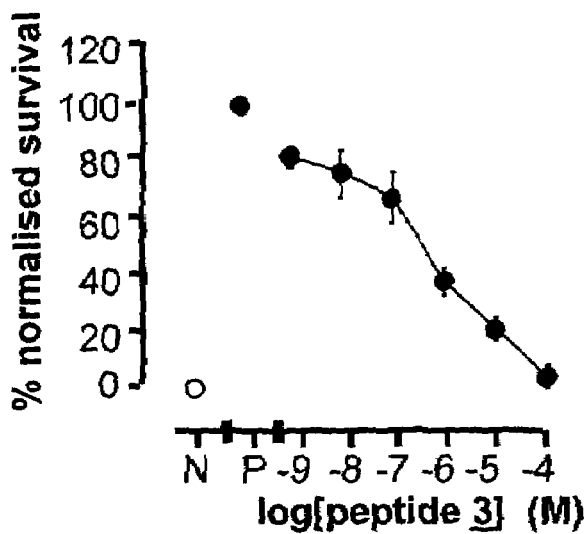
Figure 15A:
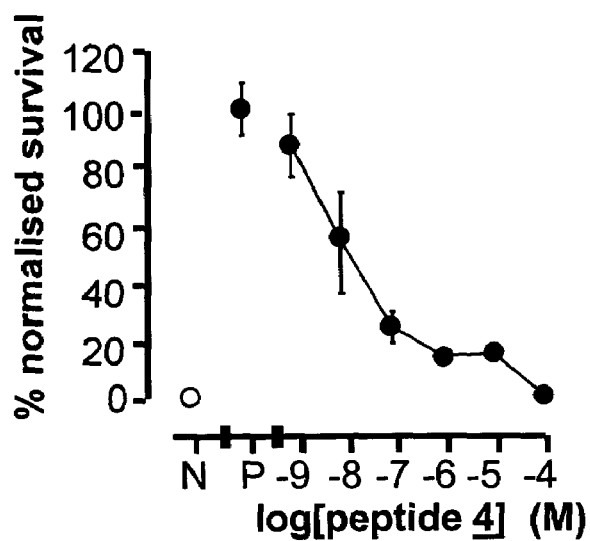
FIGS. 15a–c show the effects of peptide 4 (15a), peptide 5 (15b) and peptide 6 (15c), respectively, on VEGF-C mediated cell survival in the VEGFR-2 bioassay after 48 hours in culture.
Figure 15B:
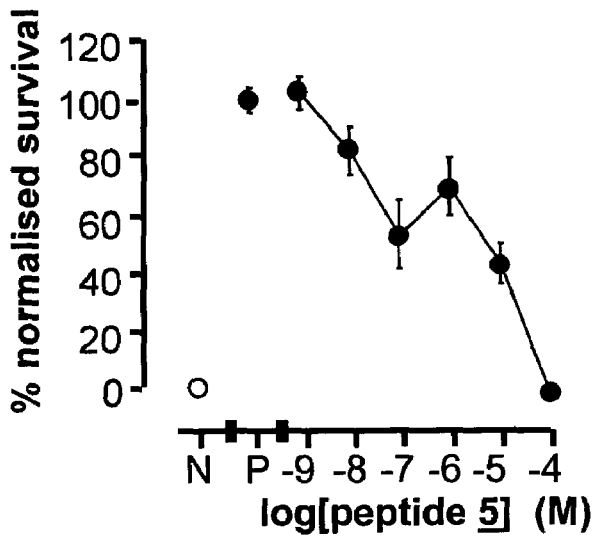
Figure 15C:
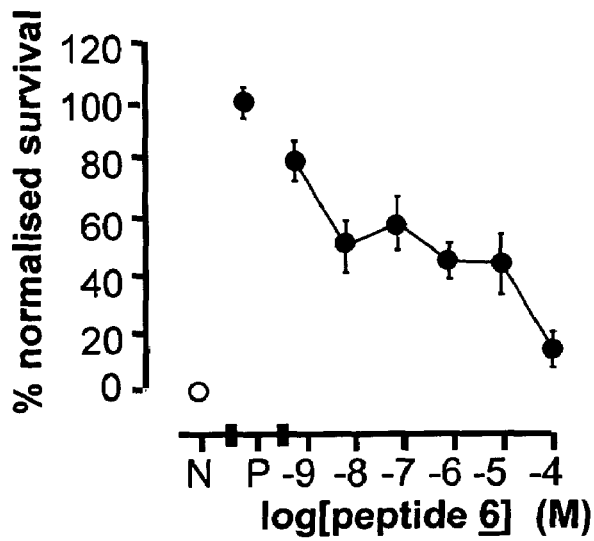

As shown in FIGS. 14a–c, respectively, the monomeric monocyclic peptides 1, 2 and 3 each were found to inhibit VEGF-C-induced VEGFR-2-mediated cell survival. The data differ somewhat from that obtained against VEGF-D-induced VEGFR-3-mediated cell survival in Example 12 above, in that the most effective inhibitor is peptide 3 (inhibition at $10^{-4}$ M: peptide 1: 48±10%; peptide 2: 67±10%; peptide 3: 93±4%). The dimeric bicyclic peptides 4, 5 and 6 (FIGS. 15a–c, respectively) also inhibited VEGF-C-induced VEGFR-2-mediated cell survival, with both peptides 4 and 5 giving near complete inhibition at $10^{-4}$ M (peptide 4: 94±2%; peptide 5: 99±1%; peptide 6: 83±6%).

Example 14

Inhibition of VEGF-C-induced VEGFR-3-mediated Cell Survival by Monomeric Monocyclic Mimetics and Dimeric Bicyclic Mimetics of Receptor Binding Loops of VEGF-D The purified monomeric monocyclic peptides 1, 2 and 3 and the dimeric bicyclic peptides 4, 5 and 6 each were tested for the ability to interfere with the activity of recombinant VEGF-C mediated by mouse VEGFR-3, using the VEGFR-3 bioassay described in Example 12 above. The assay was carried out in an analogous manner to that described in Example 12, except that 1 hour after the addition of the monomeric monocyclic peptides 1, 2 and 3 and the dimeric bicyclic peptides 4, 5 and 6 to culture wells, recombinant VEGF-CΔNΔC was added, at a concentration to produce near-maximal survival(3 ng/ml).

Figure 16A:
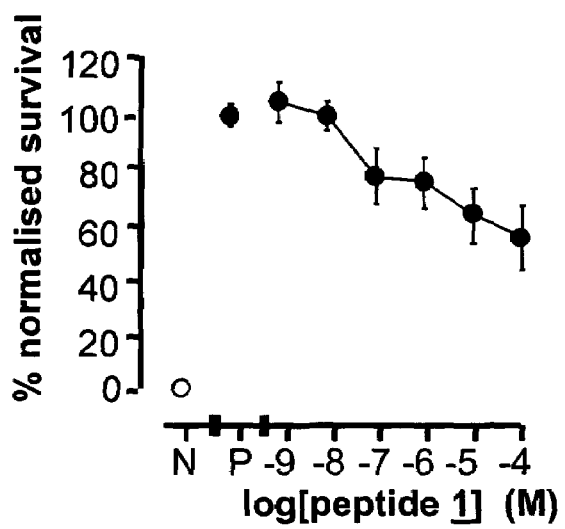
FIGS. 16a–c show the effects of peptide 1 (16a), peptide 2 (16b) and peptide 3 (16c), respectively, on VEGF-C mediated cell survival in the VEGFR-3 bioassay after 48 hours in culture.
Figure 16B:
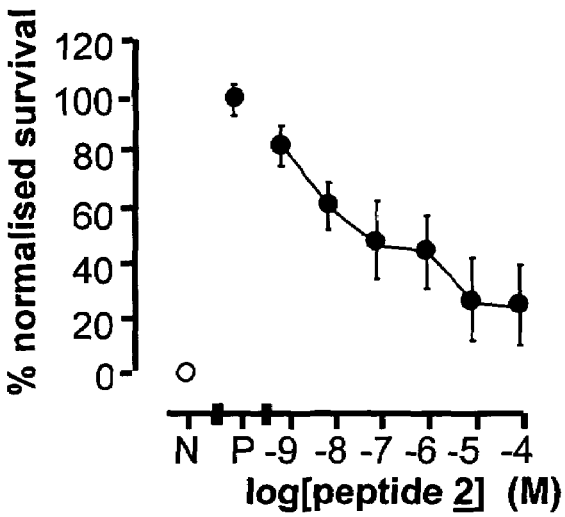
Figure 16C:
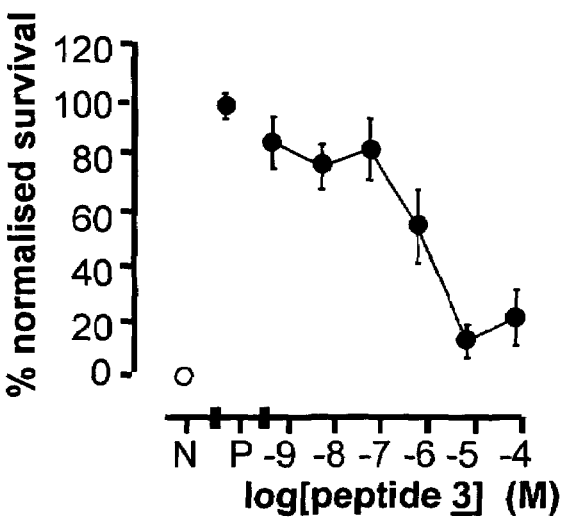
Figure 17A:
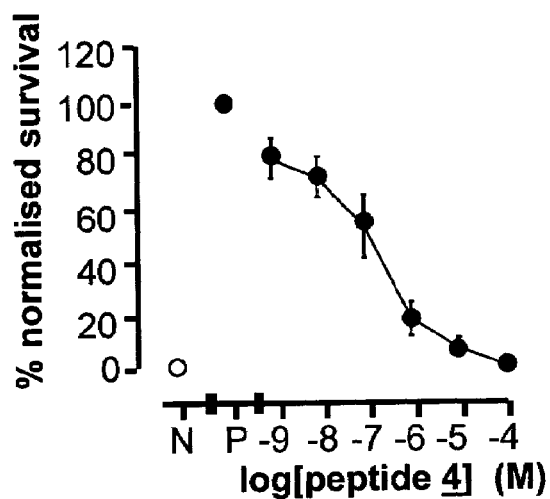
FIGS. 17a–c show the effects of peptide 4 (17a), peptide 5 (17b) and peptide 6 (17c), respectively, on VEGF-C mediated cell survival in the VEGFR-3 bioassay after 48 hours in culture.
Figure 17B:
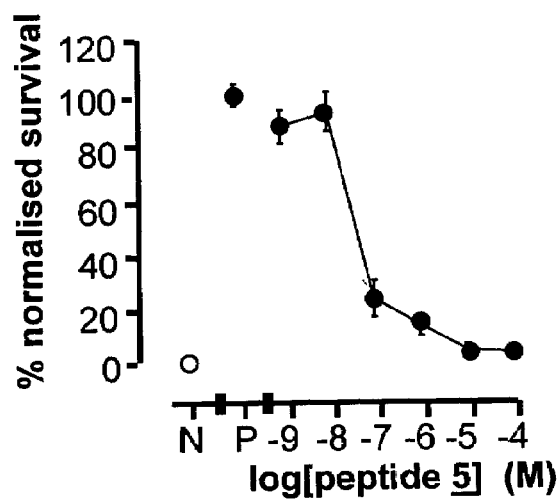
Figure 17C:
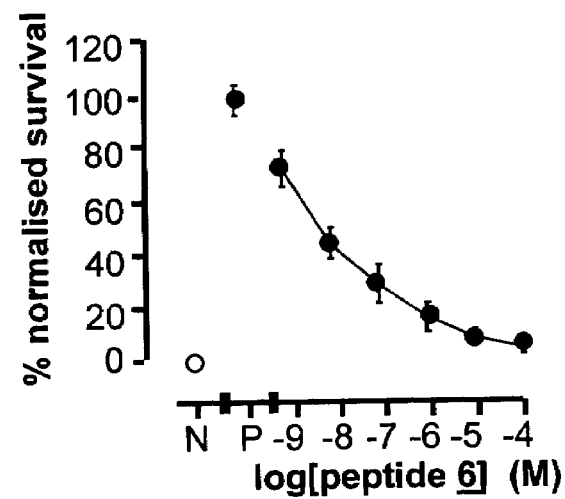

As shown in FIGS. 16a–c, respectively, the monomeric monocyclic peptides 1, 2 and 3 each were found to inhibit VEGF-C-induced VEGFR-3-mediated cell survival. Like the data obtained for VEGF-C-induced VEGFR-2-mediated cell survival described in Example 13 above, the most effective inhibitor was peptide 3 (maximal inhibition of 86±6% at $10^{-5}$ M compared to peptide 1: 46±12% at $10^{-4}$ M; peptide 2: 72±14% at $10^{-4}$ M) . All three dimeric bicyclic peptides 4, 5 and 6 (FIGS. 17a–c, respectively) were effective inhibitors of VEGF-C-induced VEGFR-3-mediated cell survival (inhibition at $10^{-4}$ M: peptide 4: 100═0%; peptide 5: 97±2%; peptide 6: 95±2%).

Example 15

Molecular Design of N- and C-terminally Shortened Analogs of Monomeric Monocyclic Peptide 3

To evaluate the importance of individual amino acid residues and the minimum cycle size required for inhibitory activity of the monomeric monocyclic peptide 3, a series of N- and C-terminally shortened peptides 7, 8 and 9 (Table 1) were designed. These monomeric monocyclic peptides, which are shortened by two residues (peptide 7). four residues (peptide 8) and five residues (peptide 9) compared to peptide 3, were designed from the model of VEGF-D in a manner analogous to that used to design the monomeric moncyclic peptides 1, 2 and 3, described in Example 2.

Example 16

Synthesis of N- and C-terminally Shortened Analogs of Monomeric Monocyclic Peptide 3

The monomeric monocyclic peptides 7–9 were synthesised from Fmoc amino acids, purified by RP-HPLC and characterized by electrospray mass spectrometry as described in Example 3.

Example 17

Inhibition of VEGF, VEGF-C and VEGF-D-induced VEGFR-2-mediated cell Survival by N- and C-terminally Shortened Analogs of Monomeric Monocyclic Peptide 3

Figure 18A:
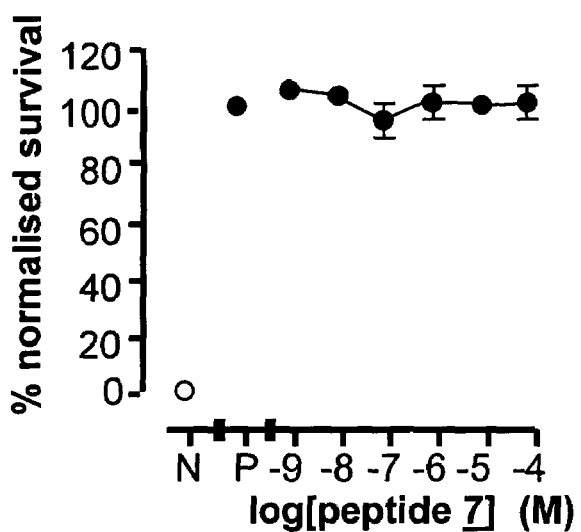
FIGS. 18a–c show the effects of peptide 7 (18a), peptide 8 (18b) and peptide 9 (18c), respectively, on VEGF mediated cell survival in the VEGFR-2 bioassay after 48 hours in culture.
Figure 18B:
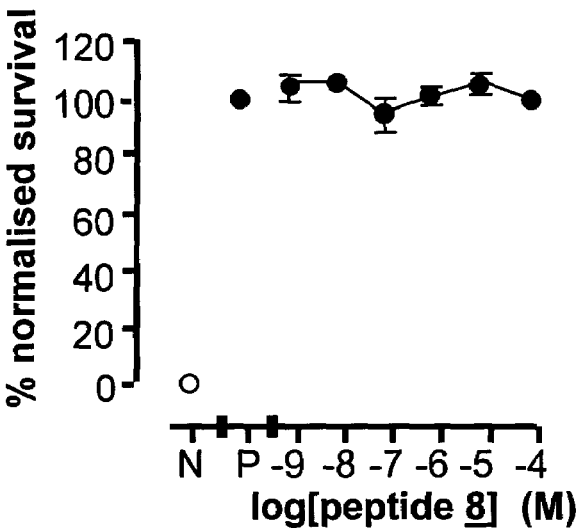
Figure 18C:
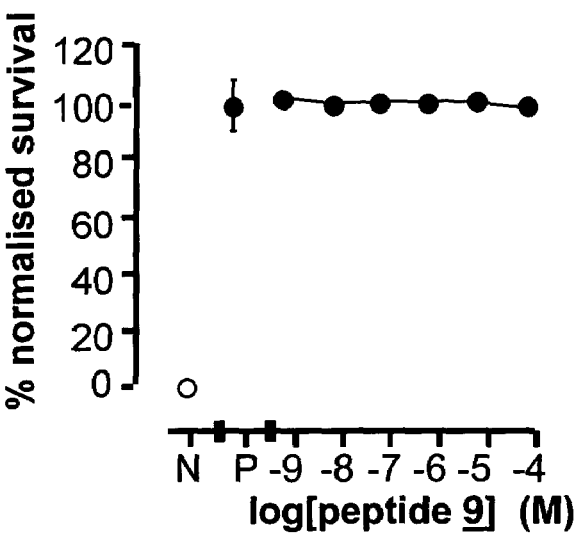
Figure 19A:
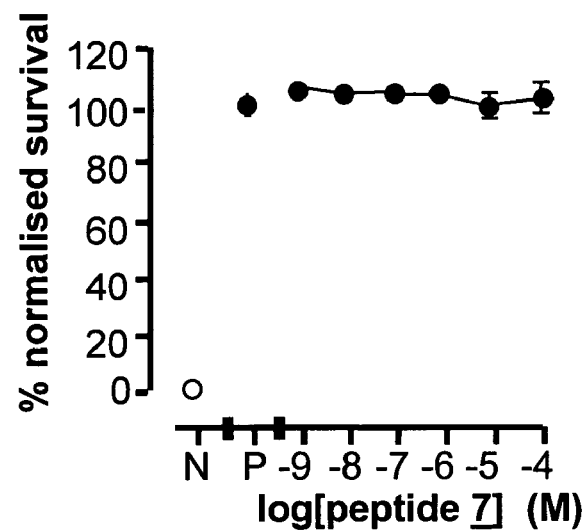
FIGS. 19a–b show the effects of peptide 7 against cell survival mediated by VEGF-C (19a) and VEGF-D (19b), respectively, in the VEGFR-2 bioassay after 48 hours in culture.
Figure 19B:
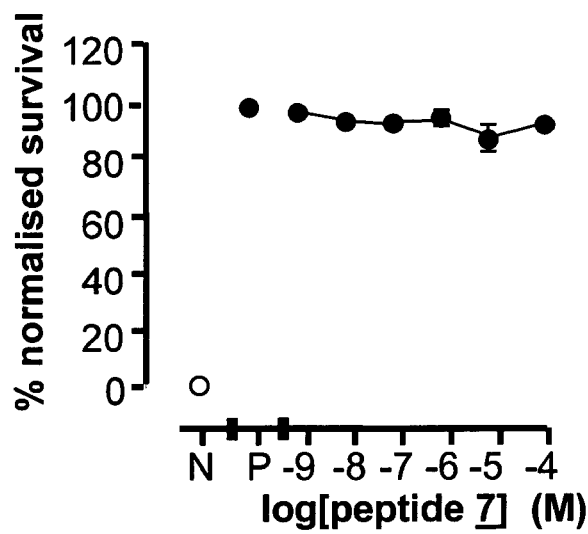

The monomeric monocyclic peptide 7 was assayed in competition with VEGF, VEGF-C$\Delta$N$\Delta$C and VEGF-D$\Delta$N$\Delta$C in the VEGFR-2 bioassay described in Example 4. Like the parent monomeric monocyclic peptide 3, peptide 7 did not inhibit the biological activity of VEGF at the concentrations tested (FIG. 18a) However, in contrast to the parent peptide 3, the absence of the N- and C-terminally derived Ile and Pro residues (peptide 7) also abolished the inhibitory activity against VEGF-C and VEGF-D through VEGFR-2 (FIGS. 19a and b). This result suggests that these two residues are either important themselves in binding to VEGFR-2 and thus preventing VEGF-C and VEGF-D from interacting with this receptor, or that they play a role in presenting adjacent residues in the loop 3-derived peptides for receptor binding. The other N- and C-terminally shortened peptide 3 analogs (peptides 8 and 9) were also without inhibitory activity over the concentration range examined when assayed in competition with VEGF in the VEGFR-2 bioassay (FIGS. 18b and c).

Example 18

Inhibition of VEGF-C and VEGF-D-induced VEGFR-3-mediated Cell Survival by N- and C-terminally Shortened Analogs of Monomeric Monocylic Peptide 3

Figure 20A:
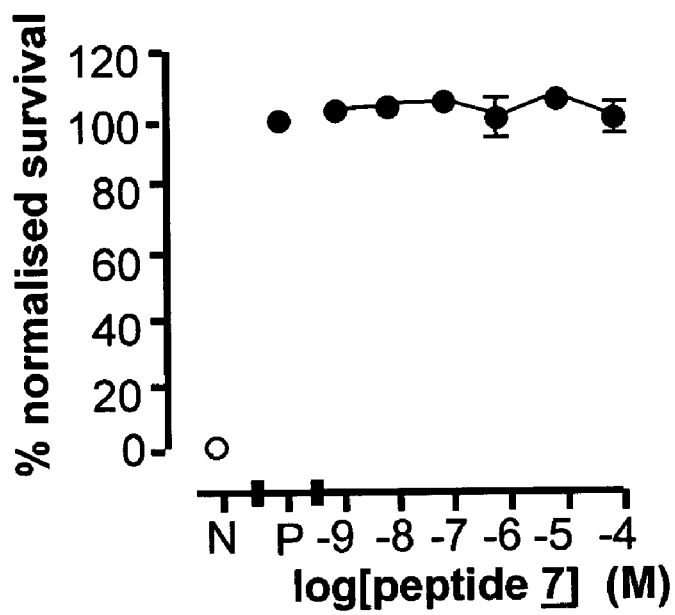
FIGS. 20a–b show the effects of peptides 7 (20a) and peptide 9 (20b), respectively, on VEGF-C mediated cell survival in the VEGFR-3 bioassay after 48 hours in culture.
Figure 20B:
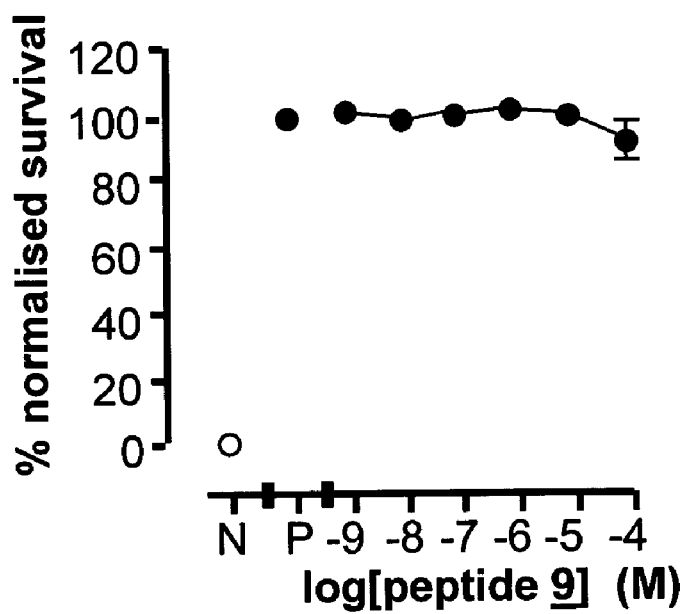
Figure 21A:
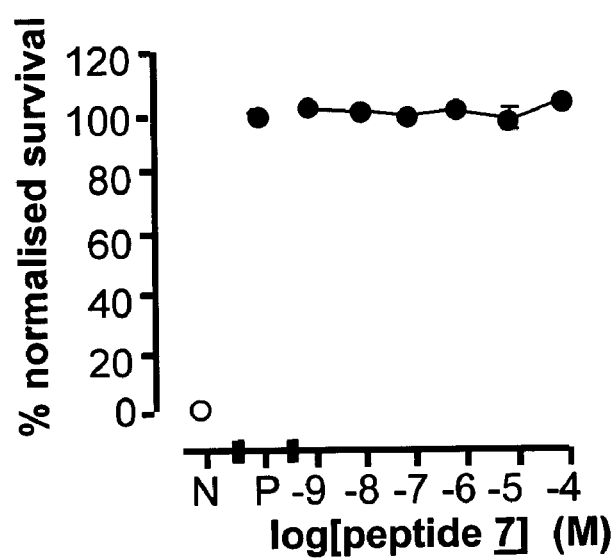
FIGS. 21a–b show the effects of peptides 7 (21a) and peptide 9 (21b), respectively, on VEGF-D mediated cell survival in the VEGFR-3 bioassay after 48 hours in culture.
Figure 21B:
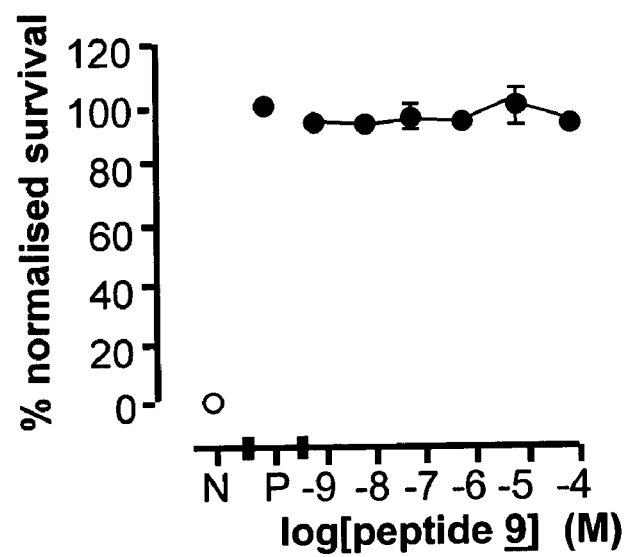

The monomeric monocyclic peptides 7 and 9 were subsequently assayed in competition with VEGF-C$\Delta$N$\Delta$C and VEGF-D$\Delta$N$\Delta$C in the VEGFR-3 bioassay described in Example 12. Neither peptide 7 nor 9 exhibited appreciable inhibition of either VEGF-C or VEGF-D activity through VEGFR-3 over the concentration range tested (FIGS. 20 and 21), similar to the situation seen with peptide 7 in the VEGFR-2 bioassay.

Example 19

Specificity of Inhibition of N- and C-terminally Shortened Analogs of Monomeric Monocyclic Peptide 3

Figure 22A:
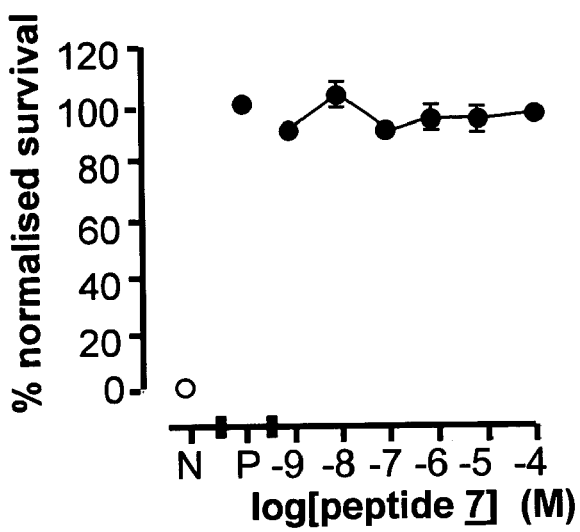
FIGS. 22a–c show the effects of peptide 7 (22a), peptide 8 (22b) and peptide 9 (22c), respectively, on IL-3 mediated cell survival/proliferation in the VEGFR-2 bioassay after 48 hours in culture.
Figure 22B:
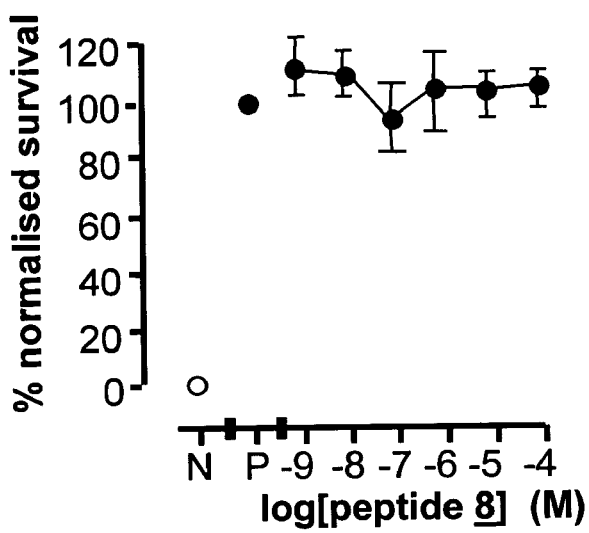
Figure 22C:
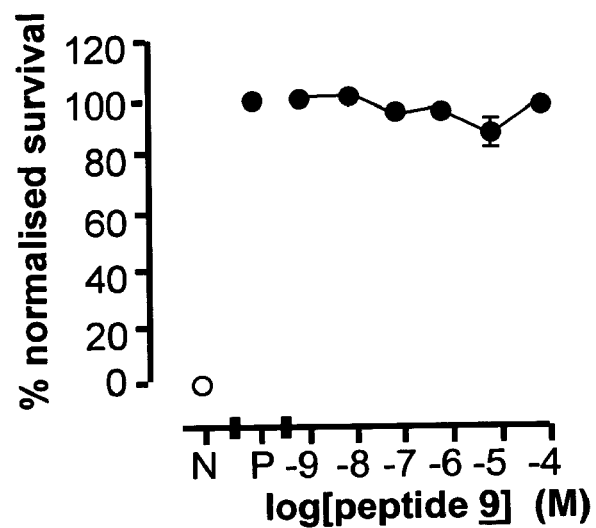

The monomeric monocyclic peptides 7–9 were assayed in competition with IL-3 in the VEGFR-2 bioassay as described in Example 6. None of the N- and C-terminally truncated peptides 7–9 caused a significant reduction in cell number of cultures grown in the presence of IL-3 (FIG. 22).

Example 20

Molecular Design of Internally Shortened Analogs of Monomeric Monocyclic Peptide 3

Because the tested analogs of monomeric monocyclic peptide 3 lacking N- and C-terminal residues were found to be devoid of inhibitory activity at either VEGFR-2 or VEGFR-3, peptides were designed in which amino acids were removed internally from the loop. Two such monomeric monocyclic peptides were designed: peptide 10, lacking an internal Thr, and peptide 11, in which Thr-Ser was been removed (Table 1).

Example 21

Synthesis of Internally Shortened Analogs of Monomeric Monocyclic Peptide 3

The monomeric monocyclic peptides 10 and 11 were synthesised from Fmoc amino acids, purified by RP-HPLC and characterized by electrospray mass spectrometry as described in Example 3.

Example 22

Inhibition of VEGF-induced VEGFR-2-mediated Cell Survival by Internally Shortened Analogs of Monomeric Monocyclic Peptide 3

Figure 23A:
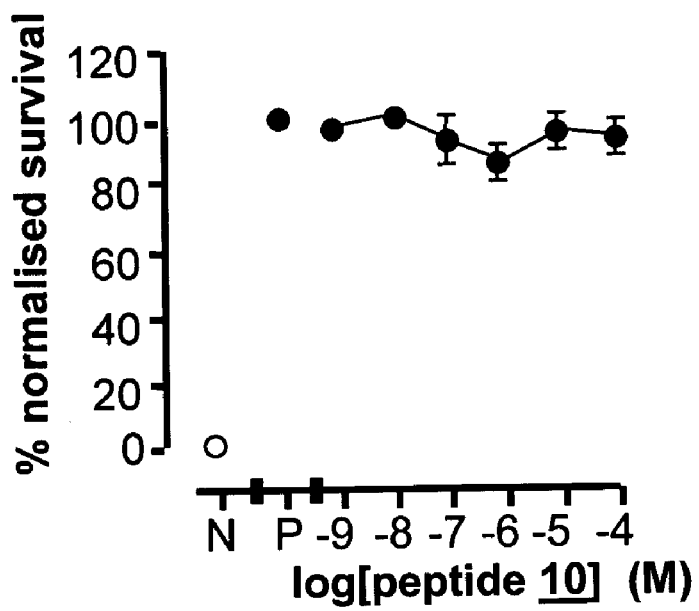
FIGS. 23a–b show the effects of peptides 10 (23a) and 11 (23b), respectively, on VEGF mediated cell survival in the VEGFR-2 bioassay after 48 hours in culture.
Figure 23B:
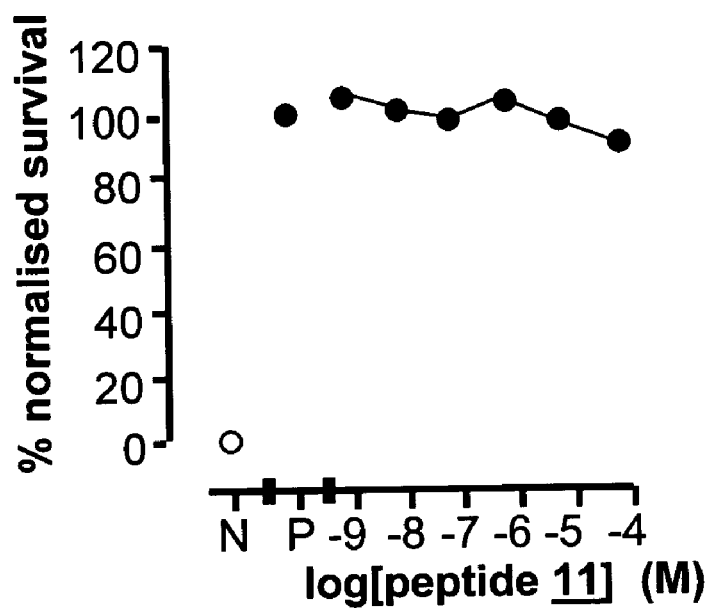

When assayed in competition with VEGF in the VEGFR-2 bioassay described in Example 4, neither of the monomeric monocylic peptides 10 nor 11 caused appreciable inhibition of VEGF-mediated cell survival over the concentration range tested (FIG. 23).

Example 23

Inhibition of VEGF-C-induced VEGFR-3-mediated Cell Survival by Internally Shortened Analogs of Monomeric Monocyclic Peptide 3

Figure 24A:
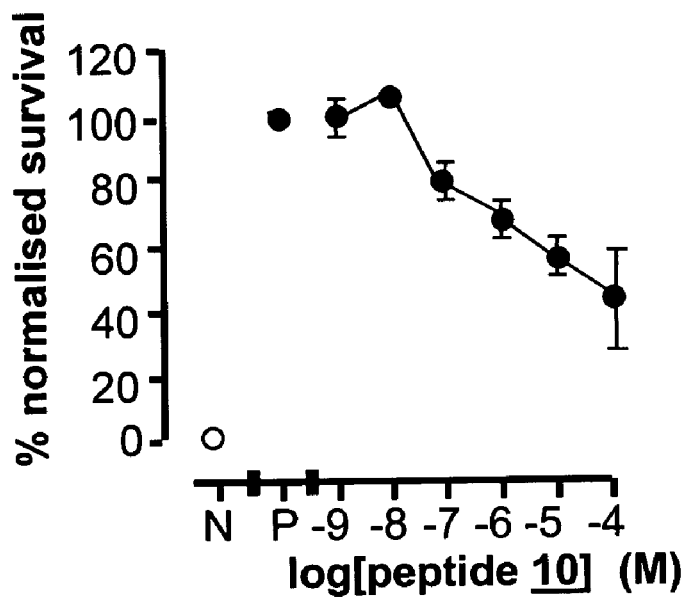
FIGS. 24a–b show the effects of peptides 10 (24a) and 11 (24b), respectively, on VEGF-C mediated cell survival in the VEGFR-3 bioassay after 48 hours in culture.
Figure 24B:
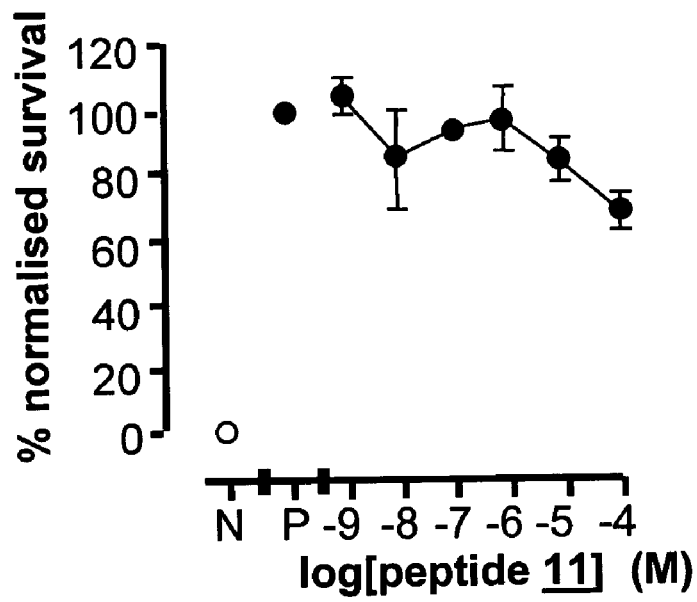

The internally shortened peptides 10 and 11 were subsequently assayed in competition with VEGF-C$\Delta$N$\Delta$C in the VEGFR-3 bioassay described in Example 12. Unlike the N- and C-terminally shortened counterparts, the internally shortened peptides retained some inhibitory activity for VEGF-C (peptide 10: 57±11% inhibition at $10^{-4}$M, FIG. 24a; peptide 11: 33±6% inhibition at $10^{-4}$M, FIG. 24b). The data suggest both that the residues absent from these sequences are not absolutely required for inhibition of VEGF-C-mediated survival through VEGFR-3, and that the resultant internally shortened peptides are still able to present at least some of the residues required for receptor binding in an appropriate conformation.

Example 24

Specificity of Inhibition of Internally Shortened Analogs of Monomeric Monocyclic Peptide 3

Figure 25A:
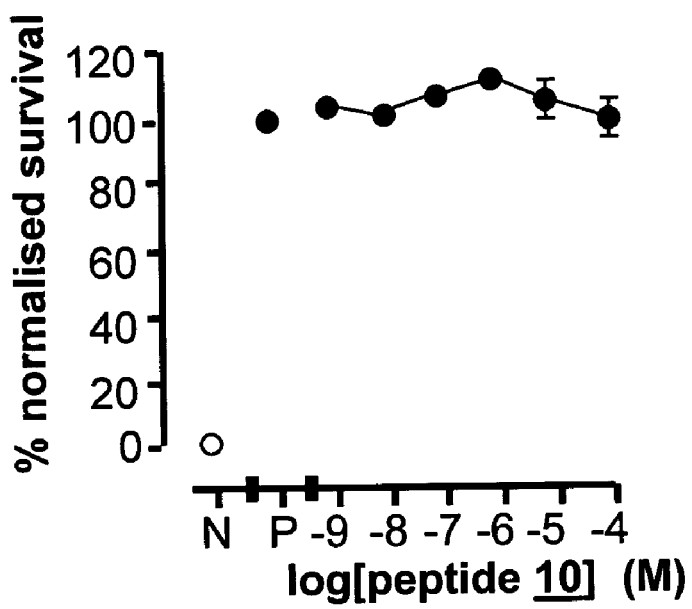
FIGS. 25a–b show the effects of peptides 10 (25a) and 11 (25b), respectively, on IL-3 mediated cell survival/proliferation in the VEGFR-2 bioassay after 48 hours in culture.
Figure 25B:
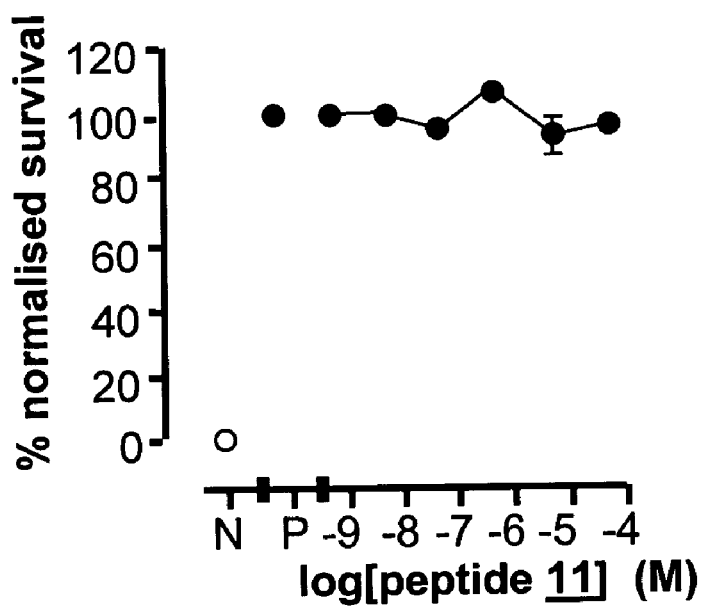

The internally shortened peptides 10 and 11 were assayed in competition with IL-3 in the VEGFR-2 bioassay as described in Example 6. Neither peptide 10 or 11 caused a significant reduction of cell number of cultures grown in the presence of IL-3 (FIG. 25). The data support the hypothesis that the inhibitory activity of these two peptide is due to a specific binding to VEGF receptors, and is not the result of non-specific inhibition of cell growth and survival.

Example 25

Synthesis of Monomeric Monocyclic Mimetics of Receptor Binding Loops of VEGF-D with Conservative Amino Acid Substitutions Synthetic peptides are synthesized based on peptides 1, 2 and 3 with conservative amino acid substitutions and cyclized as described in Example 3. Peptide 12 corresponds to peptide 1 except that serine in position 3 is replaced by threonine. Peptide 13 corresponds to peptide 1 except that serine in position 8 is replaced by threonine and threonine in position 9 is replaced by serine. Peptide 14 corresponds to peptide 1 except that glutamic acid in position 4 is replaced by asparagine, leucine in position 5 is replaced by valine and phenylalanine in position 12 is replaced by tryptophan. Peptide 15 corresponds to peptide 1 except that leucine in position 7 is replaced by arginine, and threonine in position 11 is replaced by serine. Peptide 16 corresponds to peptide 2 except glutamic acid in position 3 is replaced by asparagine, and isoleucine in position 7 is replaced by leucine. Peptide 17 corresponds to peptide 2 except that serine in position 5 is replaced by threonine. Peptide 18 corresponds to peptide 2 except that glutamic acid in position 4 is replaced by asparagine, and leucine in position 6 is replaced by phenylalanine. Peptide 19 corresponds to peptide 2 except that leucine in position 6 and isoleucine in position 7 are each replaced by valine. Peptide 20 corresponds to peptide 3 except that isoleucine in position 2 is replaced by leucine. Peptide 21 corresponds to peptide 3 except that serine in position 3 is replaced by threonine, valine in position 4 is replaced by isoleucine, and valine in position 9 is replaced by leucine. Peptide 22 corresponds to peptide 3 except that valine in position 4 is replaced by leucine, leucine in position 6 is replaced by isoleucine, and threonine in position 7 is replaced by serine. Peptide 23 corresponds to peptide 3 except that isoleucine in position 2 is replaced by valine, and serine in position 8 is replaced by threonine. The sequences of the synthetic cyclic peptides are shown in the following Table 2.

TABLE 2

Synthetic peptides based on exposed loop fragments of VEGF-D with conservative amino acid substitutions

| peptide number | sequence | sequence id no. |
|---|---|---|
| 12 | CATELGKSTNTFC | (SEQ ID NO:15) |
| 13 | CASELGKTSNTFC | (SEQ ID NO:16) |
| 14 | CASDVGKSTNTWC | (SEQ ID NO:17) |
| 15 | CASELGRSTNSFC | (SEQ ID NO:18) |
| 16 | CNDESLLC | (SEQ ID NO:19) |
| 17 | CNEETLIC | (SEQ ID NO:20) |
| 18 | CNEDSFIC | (SEQ ID NO:21) |
| 19 | CNEESVVC | (SEQ ID NO:22) |
| 20 | CLSVPLTSVPC | (SEQ ID NO:23) |
| 21 | CITIPLTSLPC | (SEQ ID NO:24) |
| 22 | CISLPISSVPC | (SEQ ID NO:25) |
| 23 | CVSVPLTTVPC | (SEQ ID NO:26) |

Example 26

Synthesis of Dimeric Bicyclic Mimetics of Receptor Binding Loops of VEGF-D with Conservative Amino Acid Substitutions Synthetic peptides are synthesized based on peptides 4 and 5 with conservative amino acid substitutions, cyclized and dimerized as described in Example 8. Peptide 24 corresponds to peptide 4 except that serine in position 3 of SEQ ID NO 27 is replaced by threonine. Peptide 25 corresponds to peptide 4 except that serine in position 8 of SEQ ID NO 28 is replaced by threonine, and threonine in position 9 of SEQ ID NO 28 is replaced by serine. Peptide 26 corresponds to peptide 4 except that glutamic acid in position 4 of SEQ ID NO 29 is replaced by asparagine, leucine in position 5 of SEQ ID NO 29 is replaced by valine and phenylalanine in position 12 of SEQ ID NO 29 is replaced by tryptophan. Peptide 27 corresponds to peptide 4 except that lysine in position 7 of SEQ ID NO 30 is replaced by arginine, and threonine in position 11 of SEQ ID NO 30 is replaced by serine. Peptide 28 corresponds to peptide 5 except that phenylalanine in position 12 of SEQ ID NO 31 is replaced by tyrosine. Peptide 29 corresponds to peptide 5 except that lysine in position 7 of SEQ ID NO 32 is replaced by arginine, and threonine in position 11 of SEQ ID NO 32 is replaced by serine. Peptide 30 corresponds to peptide 5 except that glutamic acid in position 4 of SEQ ID NO 33 is replaced by aspartic acid, and isoleucine in position 8 of SEQ ID NO 33 is replaced by leucine. Peptide 31 corresponds to peptide 5 except that serine in position 6 of SEQ ID NO 34 is replaced by threonine, and leucine in position 7 of SEQ ID NO 34 is replaced by valine. The sequences of the dimerized, bicyclic synthetic peptides are shown in the following Table 3.

TABLE 3

Synthetic peptides based on exposed loop fragments of VEGF-D with conservative amino acid substitutions

| peptide number | sequence and sequence id no. |
|---|---|
| 24 | CATELGKSTNTFCK -continued

```
Glu Ser Leu Ile Cys Met Asn Thr Ser Thr Ser Tyr Ile Ser Lys Gln
        50                  55                  60

Leu Phe Glu Ile Ser Val Pro Leu Thr Ser Val Pro Glu Leu Val Pro
 65                  70                  75                  80

Val Lys Val Ala Asn His Thr Gly Cys Lys Cys Leu Pro Thr Ala Pro
                85                  90                  95

<210> SEQ ID NO 2
<211> LENGTH: 94
<212> TYPE: PRT
<213> ORGANISM: Homo sapiens
<220> FEATURE:
<221> NAME/KEY: misc_feature
<223> OTHER INFORMATION: Amino acid residues Lys42-Asp135 of VEGF165

<400> SEQUENCE: 2

Lys Phe Met Asp Val Tyr Gln Arg Ser Tyr Cys His Pro Ile Glu Thr
 1               5                  10                  15

Leu Val Asp Ile Phe Gln Glu Tyr Pro Asp Glu Ile Glu Tyr Ile Phe
                20                  25                  30

Lys Pro Ser Cys Val Pro Leu Met Arg Cys Gly Gly Cys Cys Asn Asp
            35                  40                  45

Glu Gly Leu Glu Cys Val Pro Thr Glu Glu Ser Asn Leu Thr Met Gln
        50                  55                  60

Ile Met Arg Ile Lys Pro His Gln Gly Gln His Ile Gly Glu Met Ser
 65                  70                  75                  80

Phe Leu Gln His Asn Lys Cys Glu Cys Arg Pro Lys Lys Asp
                85                  90

<210> SEQ ID NO 3
<211> LENGTH: 73
<212> TYPE: PRT
<213> ORGANISM: Homo sapiens
<220> FEATURE:
<221> NAME/KEY: misc_feature
<223> OTHER INFORMATION: Amino acid residues Val101-Thr173 of VEGF-D

<400> SEQUENCE: 3

Val Ile Asp Glu Glu Trp Gln Arg Thr Gln Cys Ser Pro Arg Glu Thr
 1               5                  10                  15

Cys Val Glu Val Ala Ser Glu Leu Gly Lys Ser Thr Asn Thr Phe Phe
                20                  25                  30

Lys Pro Pro Cys Val Asn Val Phe Arg Cys Gly Gly Cys Cys Asn Glu
            35                  40                  45

Glu Ser Leu Ile Cys Met Asn Thr Ser Thr Ser Tyr Ile Ser Lys Gln
        50                  55                  60

Leu Phe Glu Ile Ser Val Pro Leu Thr
 65                  70

<210> SEQ ID NO 4
<211> LENGTH: 23
<212> TYPE: PRT
<213> ORGANISM: Homo sapiens
<220> FEATURE:
<221> NAME/KEY: misc_feature
<223> OTHER INFORMATION: Amino acid residues Gln113-Asp153 of VEGF165
```

```
<400> SEQUENCE: 4

Gln Gly Gln His Ile Gly Glu Met Ser Phe Leu Gln His Asn Lys Cys
1               5                   10                  15
Glu Cys Arg Pro Lys Lys Asp
            20

<210> SEQ ID NO 5
<211> LENGTH: 13
<212> TYPE: PRT
<213> ORGANISM: Homo sapiens

<400> SEQUENCE: 5

Cys Ala Ser Glu Leu Gly Lys Ser Thr Asn Thr Phe Cys
1               5                   10

<210> SEQ ID NO 6
<211> LENGTH: 8
<212> TYPE: PRT
<213> ORGANISM: Homo sapiens

<400> SEQUENCE: 6

Cys Asn Glu Glu Ser Leu Ile Cys
1               5

<210> SEQ ID NO 7
<211> LENGTH: 11
<212> TYPE: PRT
<213> ORGANISM: Homo sapiens

<400> SEQUENCE: 7

Cys Ile Ser Val Pro Leu Thr Ser Val Pro Cys
1               5                   10

<210> SEQ ID NO 8
<211> LENGTH: 17
<212> TYPE: PRT
<213> ORGANISM: Homo sapiens

<400> SEQUENCE: 8

Cys Ala Ser Glu Leu Gly Lys Ser Thr Asn Thr Phe Cys Lys Pro Pro
1               5                   10                  15
Cys

<210> SEQ ID NO 9
<211> LENGTH: 9
<212> TYPE: PRT
<213> ORGANISM: Homo sapiens

<400> SEQUENCE: 9

Cys Cys Asn Glu Glu Ser Leu Ile Cys
1               5

<210> SEQ ID NO 10
<211> LENGTH: 9
<212> TYPE: PRT
<213> ORGANISM: Homo sapiens

<400> SEQUENCE: 10

Cys Ser Val Pro Leu Thr Ser Val Cys
1               5
```

```
<210> SEQ ID NO 11
<211> LENGTH: 7
<212> TYPE: PRT
<213> ORGANISM: Homo sapiens

<400> SEQUENCE: 11

Cys Val Pro Leu Thr Ser Cys
1               5

<210> SEQ ID NO 12
<211> LENGTH: 6
<212> TYPE: PRT
<213> ORGANISM: Homo sapiens

<400> SEQUENCE: 12

Cys Val Pro Leu Thr Cys
1               5

<210> SEQ ID NO 13
<211> LENGTH: 10
<212> TYPE: PRT
<213> ORGANISM: Homo sapiens

<400> SEQUENCE: 13

Cys Ile Ser Val Pro Leu Ser Val Pro Cys
1               5                   10

<210> SEQ ID NO 14
<211> LENGTH: 9
<212> TYPE: PRT
<213> ORGANISM: Homo sapiens

<400> SEQUENCE: 14

Cys Ile Ser Val Pro Leu Val Pro Cys
1               5

<210> SEQ ID NO 15
<211> LENGTH: 13
<212> TYPE: PRT
<213> ORGANISM: synthetic construct

<400> SEQUENCE: 15

Cys Ala Thr Glu Leu Gly Lys Ser Thr Asn Thr Phe Cys
1               5                   10

<210> SEQ ID NO 16
<211> LENGTH: 13
<212> TYPE: PRT
<213> ORGANISM: synthetic construct

<400> SEQUENCE: 16

Cys Ala Ser Glu Leu Gly Lys Thr Ser Asn Thr Phe Cys
1               5                   10

<210> SEQ ID NO 17
<211> LENGTH: 13
<212> TYPE: PRT
<213> ORGANISM: synthetic construct

<400> SEQUENCE: 17

Cys Ala Ser Asp Val Gly Lys Ser Thr Asn Thr Trp Cys
1               5                   10
```

```
<210> SEQ ID NO 18
<211> LENGTH: 13
<212> TYPE: PRT
<213> ORGANISM: synthetic construct

<400> SEQUENCE: 18

Cys Ala Ser Glu Leu Gly Arg Ser Thr Asn Ser Phe Cys
1               5                   10

<210> SEQ ID NO 19
<211> LENGTH: 8
<212> TYPE: PRT
<213> ORGANISM: synthetic construct

<400> SEQUENCE: 19

Cys Asn Asp Glu Ser Leu Leu Cys
1               5

<210> SEQ ID NO 20
<211> LENGTH: 8
<212> TYPE: PRT
<213> ORGANISM: synthetic construct

<400> SEQUENCE: 20

Cys Asn Glu Glu Thr Leu Ile Cys
1               5

<210> SEQ ID NO 21
<211> LENGTH: 8
<212> TYPE: PRT
<213> ORGANISM: synthetic construct

<400> SEQUENCE: 21

Cys Asn Glu Asp Ser Phe Ile Cys
1               5

<210> SEQ ID NO 22
<211> LENGTH: 8
<212> TYPE: PRT
<213> ORGANISM: synthetic construct

<400> SEQUENCE: 22

Cys Asn Glu Glu Ser Val Val Cys
1               5

<210> SEQ ID NO 23
<211> LENGTH: 11
<212> TYPE: PRT
<213> ORGANISM: synthetic construct

<400> SEQUENCE: 23

Cys Leu Ser Val Pro Leu Thr Ser Val Pro Cys
1               5                   10

<210> SEQ ID NO 24
<211> LENGTH: 11
<212> TYPE: PRT
<213> ORGANISM: synthetic construct

<400> SEQUENCE: 24

Cys Ile Thr Ile Pro Leu Thr Ser Leu Pro Cys
1               5                   10
```

```
<210> SEQ ID NO 25
<211> LENGTH: 11
<212> TYPE: PRT
<213> ORGANISM: synthetic construct

<400> SEQUENCE: 25

Cys Ile Ser Leu Pro Ile Ser Ser Val Pro Cys
1               5                   10

<210> SEQ ID NO 26
<211> LENGTH: 11
<212> TYPE: PRT
<213> ORGANISM: synthetic construct

<400> SEQUENCE: 26

Cys Val Ser Val Pro Leu Thr Thr Val Pro Cys
1               5                   10

<210> SEQ ID NO 27
<211> LENGTH: 17
<212> TYPE: PRT
<213> ORGANISM: synthetic construct

<400> SEQUENCE: 27

Cys Ala Thr Glu Leu Gly Lys Ser Thr Asn Thr Phe Cys Lys Pro Pro
1               5                   10                  15

Cys

<210> SEQ ID NO 28
<211> LENGTH: 17
<212> TYPE: PRT
<213> ORGANISM: synthetic construct

<400> SEQUENCE: 28

Cys Ala Ser Glu Leu Gly Lys Thr Ser Asn Thr Phe Cys Lys Pro Pro
1               5                   10                  15

Cys

<210> SEQ ID NO 29
<211> LENGTH: 17
<212> TYPE: PRT
<213> ORGANISM: synthetic construct

<400> SEQUENCE: 29

Cys Ala Ser Asp Val Gly Lys Ser Thr Asn Thr Trp Cys Lys Pro Pro
1               5                   10                  15

Cys

<210> SEQ ID NO 30
<211> LENGTH: 17
<212> TYPE: PRT
<213> ORGANISM: synthetic construct

<400> SEQUENCE: 30

Cys Ala Ser Glu Leu Gly Arg Ser Thr Asn Ser Phe Cys Lys Pro Pro
1               5                   10                  15

Cys

<210> SEQ ID NO 31
<211> LENGTH: 17
<212> TYPE: PRT
<213> ORGANISM: synthetic construct
```

```
-continued

<400> SEQUENCE: 31

Cys Ala Ser Glu Leu Gly Lys Ser Thr Asn Thr Tyr Cys Lys Pro Pro
1               5                   10                  15

Cys

<210> SEQ ID NO 32
<211> LENGTH: 17
<212> TYPE: PRT
<213> ORGANISM: synthetic construct

<400> SEQUENCE: 32

Cys Ala Ser Glu Leu Gly Arg Ser Thr Asn Ser Phe Cys Lys Pro Pro
1               5                   10                  15

Cys

<210> SEQ ID NO 33
<211> LENGTH: 9
<212> TYPE: PRT
<213> ORGANISM: synthetic construct

<400> SEQUENCE: 33

Cys Cys Asn Asp Glu Ser Leu Leu Cys
1               5

<210> SEQ ID NO 34
<211> LENGTH: 9
<212> TYPE: PRT
<213> ORGANISM: synthetic construct

<400> SEQUENCE: 34

Cys Cys Asn Glu Glu Thr Val Ile Cys
1               5
```

What is claimed is:

1. A monomeric monocyclic peptide which interferes with a biological activity of at least one factor selected from the group consisting of VEGF, VEGF-C, and VEGF-D mediated by at least one receptor selected from the group consisting of VEGF receptor-2 and VEGF receptor 3, wherein the monomeric monocyclic peptide comprises a cyclic core consisting of a core sequence and a first linking group at one end of the core sequence, and a second linking group at the other end of the core sequence, wherein the core sequence consists of
   (a) a receptor-binding loop 1, 2 or 3 of VEGF-D, selected from the group consisting of SEQ ID NO:7; SEQ ID NO :10; SEQ ID NO:11; SEQ ID NO:12; SEQ ID NO:13 and SEQ ID NO:14,
   (b) a loop fragment consisting of a sequence selected from the group consisting of SEQ ID NO:5; SEQ ID NO:6; SEQ ID NO:7; SEQ ID NO:10; SEQ ID NO:11; SEQ ID NO:12; SEQ ID NO:13 and SEQ ID NO:14 with one or more conservative amino acid substitutions, or
   (c) a loop fragment consisting of a sequence selected from the group consisting of SEQ ID NO:5; SEQ ID NO:6; SEQ ID NO:7; SEQ ID NO:10; SEQ ID NO:11; SEQ ID NO:12; SEQ ID NO:13 and SEQ ID NO:14 with one or two amino acid residues deleted or inserted,
wherein the first and second linking groups are connected to form a constraint that cyclize the peptide such that receptor-binding loops 1, 2 or 3 or the corresponding loop fragment mimics a native conformation in the corresponding region of VEGF-D.

2. The monomeric monocycle peptide according to claim 1, which interferes with a biological activity of VEGF-C or VEGF-D mediated by VEGF receptor-2.

3. The monomeric monocycle peptide according to claim 1, which interferes with a biological activity of VEGF-C or VEGF-D mediated by VEGF receptor-3.

4. A monomeric, monocyclic peptide produced by a method comprising:
   obtaining a receptor-binding loop 1, 2 and 3 of VEGF-D,
   modifying the loop with one or more conservative amino acid substitutions to produce a modified loop;
   measuring beta-beta carbon separation distances on opposing antiparallel strands of the modified loop;
   selecting a modified loop with a beta-beta carbon location with a separation distance of less than 6 angstroms;
   providing a linking group in each opposing antiparallel strand at the selected beta-beta carbon location, and
   cyclizing the peptide by linking the linking groups to form a constraint that cyclizes the peptide such that receptor-binding loops 1, 2 or 3 or the corresponding loop fragment mimics a respective native conformation, wherein a monomeric, monocyclic peptide, which interferes with a biological activity of at least one factor selected from the group consisting of VEGF, VEGF-C, and VEGF-D mediated by at least one receptor selected from the group consisting of VEGF receptor-2 and VEGF receptor-3.

5. The cyclic peptide according to claim 4, wherein the method further comprises deleting at least one amino acid residue from said loop fragment prior to cyclizing the peptide, wherein the cyclic peptide interferes with a biological activity of at least one factor selected from the group consisting of VEGF, VEGF-C, and VEGF-D mediated by at least one receptor selected from the group consisting of VEGF receptor-2 and VEGF receptor-3.

6. A composition of matter comprising the monomeric monocyclic peptide according to claim 1, and at least one pharmaceutical carrier or adjuvant.

7. A composition of matter comprising the monomeric monocyclic peptide according to claim 4, and at least one pharmaceutical carrier or adjuvant.

8. A composition of matter comprising a cyclic peptide according to claim 5, and at least one pharmaceutical carrier or adjuvant.

9. A cyclic peptide comprising a peptide sequence selected from the group consisting of SEQ ID NO:7; SEQ ID NO:10; SEQ ID NO:11; SEQ ID NO:13 and SEQ ID NO:14.

10. The cyclic peptide according to claim 9, wherein said peptide is a monomeric monocyclic peptide.

11. The cyclic peptide according to claim 10, wherein said peptide interferes with a biological activity mediated by at least one receptor selected from the group consisting of VEGF receptor-2 and VEGF receptor-3.

12. The cyclic peptide according to claim 1, SEQ ID NO:5.

13. The cyclic peptide according to claim 1, consisting of SEQ ID NO:6.

14. The cyclic peptide according to claim 9, comprising SEQ ID NO:7.

15. The cyclic peptide according to claim 9, comprising SEQ ID NO:13.

16. The cyclic peptide according to claim 4, which interferes with the activity of VEGF-D and/or VEGF-C, but not VEGF, mediated by VEGF receptor-2.

17. The monomeric monocyclic peptide of claim 1, wherein the constraint maintains a beta-beta carbon separation distance between opposing anti-parallel strands of the loop or loop fragment at less than 6 angstrom.

18. The monomeric monocyclic peptide of claim 1, wherein the first or second linking group comprises 1 to 20 carbon atoms, or 1 to 10 heteroatoms, which may be straight chain or branched which contain one or more saturated, unsaturated or aromatic ring.

19. The monomeric monocyclic peptide of claim 18, wherein the hetero atom is selected from the group consisting of N, O, S, and P.

20. The monomeric monocyclic peptide of claim 1, wherein the constraint is an amide, ester, disulfide, thioether, ether, phosphate, or amine group.

21. The monomeric Monocylic peptide of claim 20, wherein the constraint is formed between an N-terminal amine and a C-terminal carboxyl of the peptide.

22. The monomeric monocyclic peptide of claim 21, wherein the constraint is formed directly via an amide bond between an N-terminal nitrogen and a C-terminal carbonyl.

23. The monomeric monocyclic peptide of claim 21, wherein the constraint is formed indirectly via a spacer group.

24. The monomeric monocyclic peptide of claim 23, wherein the spacer group is 4-amino carboxylic acid.

25. The monomeric monocyclic peptide of claim 20, wherein the constraint is a covalent bond between side chains of two amino acid residues of the peptide.

26. The monomeric monocyclic peptide of claim 1, wherein the constraint is an amide bond between a lysine residue and an aspartic acid or glutamic acid residue, a disulfide bond between two cysteine residues, or a thioether bond between a cysteine residue and a 4-halogenated amino acid residue.

27. The monomeric monocyclic peptide of claim 26, wherein the constraint is a disulfide bond formed between two cysteine residues.

28. The monomeric monocyclic peptide of claim 25, wherein residues contributing the side chains may be derived from the loop sequence itself, or may be Incorporated into or added on to the loop sequence.

29. The monomeric monocylic peptide of claim 20, wherein the constraint is an amide bond between a side chain of an amino acid and the C-terminal carboxyl or N-terminal amine.

30. The monomeric moncyclic peptide of claim 29, wherein residue contributing the side chain may be derived from the loop sequence itself, or may be incorporated into or added on to the loop sequence.

31. The monomeric monocyclic peptide of claim 1, wherein the core sequence consists of 4 to 11 amino acid residues.

32. The monomeric monocyclic peptide of claim 31, wherein the core sequence consists of 6 to 11 amino acid residues.

33. A monomeric, monocyclic peptide according to claim 4, wherein the linking group is a cysteine residue, and the peptide is cyclized by oxidizing the cysteine residues to form a disulfide bridge between strands.

* * * * *